(12) United States Patent
Xing

(10) Patent No.: US 10,584,108 B2
(45) Date of Patent: Mar. 10, 2020

(54) THERAPEUTIC COMPOUNDS AND METHODS OF USE THEREOF

(71) Applicant: KUALITY HERBCEUTICS LLC, Gainesville, FL (US)

(72) Inventor: Chengguo Xing, Gainesville, FL (US)

(73) Assignee: Kuality Herbceutics LLC, Gainesville, FL (US)

(*) Notice: Subject to any disclaimer, the term of this patent is extended or adjusted under 35 U.S.C. 154(b) by 0 days.

(21) Appl. No.: 15/572,439

(22) PCT Filed: May 9, 2016

(86) PCT No.: PCT/US2016/031474
§ 371 (c)(1),
(2) Date: Nov. 7, 2017

(87) PCT Pub. No.: WO2016/179587
PCT Pub. Date: Nov. 10, 2016

(65) Prior Publication Data
US 2018/0134679 A1 May 17, 2018

Related U.S. Application Data

(60) Provisional application No. 62/158,369, filed on May 7, 2015.

(51) Int. Cl.
| C07D 317/50 | (2006.01) |
| C07D 309/32 | (2006.01) |
| C07D 407/06 | (2006.01) |
| C07D 317/54 | (2006.01) |
| A61P 35/00 | (2006.01) |
| C07C 49/657 | (2006.01) |

(52) U.S. Cl.
CPC ............ *C07D 309/32* (2013.01); *A61P 35/00* (2018.01); *C07C 49/657* (2013.01); *C07D 317/54* (2013.01); *C07D 407/06* (2013.01); *C07C 2601/14* (2017.05); *C07C 2602/08* (2017.05)

(58) Field of Classification Search
CPC .................................................. C07D 317/50
USPC .................................. 549/434, 445; 514/469
See application file for complete search history.

(56) References Cited

U.S. PATENT DOCUMENTS

| 2,524,107 A * | 10/1950 | Hedenburg .......... C07D 317/54 549/446 |
| 4,511,391 A * | 4/1985 | Serban .................. A01N 43/12 504/176 |
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,585,386 A | 12/1996 | Rosenbaum |
| 5,936,128 A | 8/1999 | Ellsworth et al. |
| 6,303,157 B1 | 10/2001 | Ono et al. |
| 2003/0105159 A1 | 6/2003 | McCleary et al. |
| 2004/0029831 A1 | 2/2004 | Ono et al. |
| 2006/0121132 A1 | 6/2006 | Asakawa et al. |
| 2016/0279184 A1 | 9/2016 | Xing et al. |

FOREIGN PATENT DOCUMENTS

| CN | 1557388 A | 12/2004 |
| CN | 1263476 C | 7/2006 |
| GB | 2410435 A | 8/2005 |
| WO | 2002091966 A1 | 11/2002 |
| WO | 2005067950 A1 | 7/2005 |
| WO | 2015070226 A1 | 5/2015 |

OTHER PUBLICATIONS

Jyothi et al., "An efficient synthesis, etc.," Indian Journal of Chemistry, 47B, pp. 630-632. (Year: 2008).*
Fujii et al., "Structure-activity, etc.," CA 73:2132. (Year: 1970).*
Poe et al., "A Boron-Based, etc.," Angew. Chem. Int. Ed. 50, 4189-4192. (Year: 2011).*
Magar et al., "Ruthenium(II)-Cataylzed, etc.," Adv. Synth. Catal, 356, 3422-3432. (Year: 2014).*
Tamura, "Nonsteroidal Antiinflammatory, etc.," Journal of Medicinal Chemistry, 20(5), 709-714. (Year: 1977).*
Jaffe et a. "In vivo inhibition, etc.," CA 70:2714. (Year: 1969).*
Anke, et al., "Kava Hepatotoxicity: Are we any closer to the truth?", Planta Med 70, 193-196 (2004).
Burns, et al., "Do changes in cigarette design influence the rise in adenocarcinoma of the lung", Cancer Causes Control 22, 13-22 (2011).
Chiaverotti, et al., "Dissociation of epithelial and neuroendocrine carcinoma lineages in the transgenic adenocarcinoma of mouse prostate model of prostate cancer", Am J Pathol 172(1), 236-246 (2008).
Cohen, et al., "Chemoprevention of lung cancer", Curr Opin Pulm Med 10, 279-283 (2004).
Crampsie, et al., "Phenylbutyl isoselenocyanate modulates phase I and II enzymes and inhibits 4-(methylnitrosamino)-1-(3-pyridyl)-1-butanone-induced DNA adducts in mice", Cancer Prev Res 4, 1884-1894 (2011).
Disilvestro, et al., "Kava feeding in rats does not cause liver injury nor enhance galactosamine-induced hepatitis", Food Chem Toxicol 45, 1293-1300 (2007).
Fatima, et al., "Cytotoxic activity of (S)-goniothalamin and analogues against human cancer cells", Bioorganic & Medicinal Chemistry 14(3), 622-631 (2006).
Greenberg, et al., "Prostate cancer in a transgenic mouse", PNAS 92(8), 3439-3443 (1995).
Guo, et al., "Analysis of gene expression changes of drug metabolizing enzymes in the livers of F344 rats following oral treatment with kava extract", Food Chem Toxicol 47, 433-442 (2009).

(Continued)

Primary Examiner — Patricia L Morris
(74) Attorney, Agent, or Firm — Viksnins Harris Padys Malen LLP

(57) ABSTRACT

The invention provides compounds that are useful for treating or preventing cancer.

8 Claims, No Drawings

(56) References Cited

OTHER PUBLICATIONS

Guo, et al., "Gene expression profiling in male B6C3F1 mouse livers exposed to kava identifies—changes in drug metabolizing genes and potential mechanisms linked to kava toxicity", Food Chem Toxicol 48, 686-696 (2010).
Hecht, "Progress and challenges in selected areas of tobacco carcinogenesis", Chem Res Toxicol 21, 160-171 (2008).
Hecht, "Biochemistry, biology, and carcinogenicity of tobacco-specific N-nitrosamines", Chem Res Toxicol 11, 559-603 (1998).
Hecht, et al., "Chemoprevention of lung carcinogenesis in addicted smokers and ex-smokers", Nat Rev Cancer 9, 476-488 (2009).
Hecht, "Lung carcinogenesis by tobacco smoke", Int J Cancer 131, 2724-2732 (2012).
Hou, et al., "Structure-based optimization of click-based histone deacetylase inhibitors", European Journal of Medicinal Chemistry 46(8), 3190-3200 (2011).
Huss, et al., "Origin of androgen-insensitive poorly differentiated tumors in the transgenic adenocarcinoma of mouse prostate model", Neoplasia 9(11), 938-950 (2007).
Jhoo, et al., "In Vitro Cytotoxicity of Nonpolar Constituents from Different Parts of Kava Plant (*Piper methysticum*)", J Agric Food Chem 54, 3157-3162 (2006).
Johnson, et al., "Chemopreventive Effect of Kava on 4-(Methylnitrosamino)-1-(3-pyridyl)-1-butanone plus Benzo[a]pyrene-Induced Lung Tumorigenesis in A/J Mice", Cancer Prev Res 1, 430-438 (2008).
Johnson, et al., "Lung Tumorigenesis Suppressing Effects of a Commercial Kava Extract and Its Selected Compounds in A/J Mice", American Journal of Chinese Medicine, vol. 39 (4), 727-742 (2011).
Lao, et al., "Formation and accumulation of pyridyloxobutyl DNA adducts in F344 rats chronically treated with 4-(methylnitrosamino)-1-(3-pyridyl)-1-butanone and enantiomers of its metabolite, 4-(methylnitrosamino)-1-(3-pyridyl)-1-butanol", Chem Res Toxicol 20, 235-245 (2007).
Lao, et al., "Quantitation of pyridyloxobutyl DNA adducts of tobacco-specific nitrosamines in rat tissue DNA by high-performance liquid chromatography-electrospray ionization-tandem mass spectrometry", Chem Res Toxicol 19, 674-682 (2006).
Laporte, "Neurocognitive effects of kava (*Piper methysticum*): a systematic review", Hum Psychopharmacol 26, 102-111 (2011).
Lebot, et al., "Detection of flavokavins (A, B, C) in cultivars of kava (*Piper methysticum*) using high performance thin layer chromatography (HPTLC)", Food Chem 151, 554-560 (2014).
Leitzman, et al., "Kava blocks 4-(methylnitrosamino)-1-(3-pyridyl)-1-butanone-induced lung tumorigenesis in association with reducing O6-methylguanine DNA adduct in A/J mice", Cancer Prev Res (Phila), 7(1), 86-96 (2014).
Li, et al., "Methysticin and 7,8-Dihydromethysticin are Two Major Kavalactones in Kava Extract to Induce CYP1A1", Toxicological Sciences 124(2), 388-399 (2011).
Lin, et al., "Flavokawain B inhibits growth of human squamous carcinoma cells: Involvement of apoptosis and cell cycle dysregulation in vitro and in vivo", J Nutr Biochem 23, 368-378 (2012).
Liu, et al., "Reduced lung tumorigenesis in human methylguanine DNA—methyltransferase transgenic mice achieved by expression of transgene within the target cell", Carcinogenesis 20, 279-284 (1999).
Loechler, et al., "In vivo mutagenesis by O6-methylguanine built into a unique site in a viral genome", Proc Natl Acad Sci 81, 6271-6275 (1984).
Malkinson, "Primary lung tumors in mice as an aid for understanding, preventing, and treating human adenocarcinoma of the lung", Lung Cancer 32, 265-279 (2001).
Martin, et al., "Measuring the chemical and cytotoxic variability of commercially available kava (*Piper methysticum* G. Forster).", PLoS One 9(11), e111572, 7 pages (2014).
Morse, et al., "Effects of aromatic isothiocyanates on tumorigenicity, O6-methylguanine formation, and metabolism of the tobacco-specific nitrosamine 4-(methylnitrosamino)-1-(3-pyridyl)-1-butanone in A/J mouse lung", Cancer Res 49, 2894-2897 (1989).
Morse, et al., "Effects of indole-3-carbinol on lung tumorigenesis and DNA methylation induced by 4-(methylnitrosamino)-1-(3-pyridyl)-1-butanone (NNK) and on the metabolism and disposition of NNK in A/J mice", Cancer Res 50(9), 2613-2617 (1990).
Murphy, et al., "Effects of phenobarbital and 3-methylcholanthrene induction on the formation of three glucuronide metabolites of 4-(methylnitrosamino)-1-(3-pyridyl)-1-butanone, NNK", Chemico-Biological Interactions 103(3), 153-166 (1997).
Narayanapillai, et al., "Dihydromethysticin from kava blocks tobacco carcinogen 4-(methylnitrosamino)-1-(3-pyridyl)-1-butanone-induced lung tumorigenesis and differentially reduces DNA damage in A/J mice", Carcinogenesis vol. 35(10), 2365-2372 (2014).
Narayanapillai, et al., "Flavokawains A and B in Kava, not Dihydromethysticin, Potentiate Acetaminophen-Induced Hepatotoxicity in C57BL/6 Mice", Chemical Research in Toxicology 27, 1871-1876 (2014).
National Toxicology Program, "Toxicology and carcinogenesis studies of kava kava extract (CAS No. 9000-38-8) in F344/N rats and B6C3F1 mice (Gavage Studies).", National Toxicology Program Tech Rep Ser (571), 1-186 (2012).
Ni, et al., "Quantitation of 13 heterocyclic aromatic amines in cooked beef, pork, and chicken by liquid chromatography-electrospray ionization/tandem mass spectrometry", Journal of Agricultural and Food Chemistry, 56 (1), 68-78 (2008).
Nishikawa, et al., "Induction of colon tumors in C57BL/6J mice fed MelQx, IQ, or PhIP followed by dextran sulfate sodium treatment", Journal of Society of Toxicology 84(2), 243-248 (2005).
O'Donnell, et al., "Quantitative analysis of early chemically-induced pulmonary lesions in mice of varying susceptibilities to lung tumorigenesis", Cancer Lett 241, 197-202 (2006).
Patent Cooperation Treaty, International Searching Authority, Search Report and Written Opinion for PCT/US16/31474, 9 pages (dated Aug. 8, 2016).
Peterson, et al., "O6-methylguanine is a critical determinant of 4-(methylnitrosamino)-1-(3-pyridyl)-1-butanone tumorigenesis in A/J mouse lung", Cancer Res 51, 5557-5564 (1991).
Peterson, et al., "Pyridyloxobutyl DNA adducts inhibit the repair of O6-methylguanine", Cancer Res 53, 2780-2785 (1993).
Peterson, et al., "Quantitation of microsomal alpha-hydroxylation of the tobacco-specific nitrosamine, 4-(methylnitrosamino)-1-(3-pyridyl)-1-butanone", Cancer Res 51, 5495-5500 (1991).
Peterson, et al., "Role of aldehydes in the toxic and mutagenic effects of nitrosamines", Chem Res Toxicol 26, 1464-1473 (2013).
Pittler, et al., "Efficacy of kava extract for treating anxiety: systematic review and meta-analysis", J Clin Psychopharmacol 20(1), 84-89 (2000).
Prokopczyk, et al., "Effects of dietary 1,4-phenylenebis(methylene)selenocyanate on 4-(methylnitrosamino)-1-(3-pyridyl)-1-butanone-induced DNA adduct formation in lung and liver of A/J mice and F344 rats", Carcinogenesis 17, 749-753 (1996).
Reagan-Shaw, et al., "Dose translation from animal to human studies revisited", FASEB J 22, 659-661 (2008).
Rowe, et al., "Are mould hepatotoxins responsible for kava hepatotoxicity?", Res 26, 1768-1770 (2012).
Sarris, et al., "Kava in the treatment of generalized anxiety disorder: a double-blind, randomized, placebo-controlled study", J Clin Psychopharmacol 33(5), 643-648 (2013).
Sarris, "St. John's wort and Kava in treating major depressive disorder with comorbid anxiety: a randomised double-blind placebo-controlled pilot trial", Hum Psychopharmacol 24, 41-48 (2009).
Sarris, et al., "The Kava Anxiety Depression Spectrum Study (KADSS): a randomized, placebo-controlled crossover trial using an aqueous extract of *Piper methysticum*", Psychopharmacology (Berl) 205, 399-407 (2009).
Savard, et al., "Regiospecific syntheses of quinones using vinylketene acetals derived from unsaturated esters", Tetrahedron Lett 20, 4911-4914 (1979).
Shaik, et al., "Identification of methysticin as a potent and non-toxic NF-kB inhibitor from kava, potentially responsible for kava's

(56) References Cited

OTHER PUBLICATIONS chemopreventive activity", Bioorganic & Medicinal Chemistry Letter, 19, 5732-5736; Supporting Information, 9 pages (2009).
Smissman, et al., "The Synthesis of 3-Alkoxy-cis-2-trans-4-unsaturated Acids", J Org Chem 29, 3161-3165 (1964).
Sorrentino, et al., "Safety of ethanolic kava extract: Results of a study of chronic toxicity in rats", Phytomedicine 13, 542-549 (2006).
Sreekanth, et al., "Dihydromethysticin from kava blocks tobacco carcinogen 4-(methylnitrosamino)-1-(3-pyridyl)-1-butanone-induced lung tumorigenesis and differentially reduces DNA damage in A/J mice", Carcinogenesis 35(10), 2365-2372 (2014).
Sturla, et al., "Mass spectrometric analysis of relative levels of pyridyloxobutylation adducts formed in the reaction of DNA with a chemically activated form of the tobacco-specific carcinogen 4-(methylnitrosamino)-1-(3-pyridyl)-1-butanone", Chem Res Toxicol 18, 1048-1055 (2005).
Tang, et al., "Flavokawain B, a kava chalcone, induces apoptosis via up-regulation of death-receptor 5 and Bim expression in androgen receptor negative, hormonal refractory prostate cancer cell lines and reduces tumor growth", Int J Cancer 127(8), 1758-1768 (2010).
Tang, et al., "Gene expression signatures associated with suppression of TRAMP prostate carcinogenesis by a kavalactone-rich Kava fraction", Mol. Carcinog., doi:10.1002/mc.22469 (2016).
Teschke, et al., "Contaminant hepatotoxins as culprits for kava hepatotoxicity—fact or fiction?", Phytother Res 27, 472-474 (2013).
Teschke, et al., "Kava hepatotoxicity: a clinical survey and critical analysis of 26 suspected cases", Eur J Gastroenterol Hepatol 20, 1182-1193 (2008).
Teschke, et al., "Kava hepatotoxicity: regulatory data selection and causality assessment", Dig Liver Dis 41, 891-901 (2009).
Triolet, et al., "Reduction in Colon Cancer Risk by Consumption of Kava or Kava Fractions in Carcinogen-Treated Rats", Nutrition and Cancer 64(6), 838-846 (2012).
Upadhyaya, et al., "Comparative levels of O6-methylguanine, pyridyloxobutyl-, and pyridylhydroxybutyl-DNA adducts in lung and liver of rats treated chronically with the tobacco-specific carcinogen 4-(methylnitrosamino)-1-(3-pyridyl)-1-butanone", Drug Metab Dispos 37, 1147-1151 (2009).
Upadhyaya, et al., "Quantitation of pyridylhydroxybutyl-DNA adducts in liver and lung of F-344 rats treated with 4-(methylnitrosamino)-1-(3-pyridyl)-1-butanone and enantiomers of its metabolite 4-(methylnitrosamino)-1-(3-pyridyl)-1-butanol", Chem Res Toxicol 21, 1468-1476 (2008).
Upadhyaya, et al., "Tumorigenicity and metabolism of 4-(methylnitrosamino)-1-(3-pyridyl)-1-butanol enantiomers and metabolites in the A/J mouse", Carcinogenesis 20, 1577-1582 (1999).
Urban, et al., "Formation and repair of pyridyloxobutyl DNA adducts and their relationship to tumor yield in A/J mice", Chem Res Toxicol 25, 2167-2178 (2012).
Wang, et al., "CYP17 gene polymorphisms and prostate cancer risk: a meta-analysis based on 38 independent studies", Prostate 71(11), 1167-1177 (2011).
Yang, et al., "Kava extract, an herbal alternative for anxiety relief, potentiates acetaminophen-induced cytotoxicity in rat hepatic cells", Phytomedicine 18, 592-600 (2011).
Zhou, et al., "Flavokawain B, the hepatotoxic constituent from kava root, induces GSH-sensitive oxidative stress through modulation of IKK/NF-kappaB and MAPK signaling pathways", FASEB J 24, 4722-4732 (2010).
Zi, et al., "Flavokawain A, a novel chalcone from kava extract, induces apoptosis in bladder cancer cells by involvement of Bax protein-dependent and mitochondria-dependent apoptotic pathway and suppresses tumor growth in mice", Cancer Res 65, 3479-3486 (2005).
Puppala, et al., "Pilot in Vivo Structure-Activity Relationship of Dihydromethysticin in Blocking 4-(Methylnitrosamino)-1-(3-pyridyl)-1-butanone-Induced O6-Methylguanine and Lung Tumor in A/J Mice", J Med Chem 60, 7935-7920 (2017).
Zhang, et al., "Molluscicidal activity of *Aglaia duperreana* and the constituents of its twigs and leaves", Fitoterapia 83, 1081-1086 (2012).
Huan, Y , et al., "Research Progress on Kava", Chinese Journal of Tropical Agricultural 30(11), 68-71, (2010). [English Abstract].
Kava Kava , "Summary of Data for Chemical Selection", ntp.niehs.nih.gov/ntp/htdocs/chem._background/exsumpdf/kava_508.pdf, 13 pages (1998).
Xuan, T , et al., "Efficacy of extracting solvents to chemical components of kava (*Piper methysticum*) roots", Journal of Natural Medicines 62(2), 188-194 (2007).

* cited by examiner

THERAPEUTIC COMPOUNDS AND METHODS OF USE THEREOF

CROSS-REFERENCE TO RELATED APPLICATION(S)

This application claims priority from U.S. Provisional Application No. 62/158,369, filed May 7, 2015, which application is herein incorporated by reference.

GOVERNMENT FUNDING

This invention was made with government support under R01-CA142649 awarded by the National Cancer Institute/National Institutes of Health. The government has certain rights in the invention.

BACKGROUND OF THE INVENTION

Lung cancer is the leading cause of malignancy-related mortality because of its high incidence and the lack of effective treatments. Since tobacco usage contributes to 85-90% of its development, tobacco cessation is the most straightforward strategy for reducing lung cancer incidence and mortality. However, because of the addictive nature of nicotine in tobacco, limited progress has been achieved in reducing tobacco usage. An alternative approach is to block or slow down tobacco carcinogen-induced lung cancer development via chemoprevention (Hecht et al., Nat. Rev. Cancer 2009; 9:476-88). Although a number of compounds have been identified as potential chemopreventive agents against lung tumorigenesis in animal models, their moderate in vivo efficacy leaves ample room for improvement and introduces significant challenges for clinical application/evaluation. In addition, there are very limited successes in cancer chemoprevention relative to cancer therapy.

(+)-Dihydromethysticin can effectively block NNK-induced lung tumorigenesis by reducing NNK-induced DNA damage, with $O^6$-mG being the most carcinogenic damage; this damage can be inhibited by (+)-dihydromethysticin (Leitzman P, et al., *Cancer Prevention Research* (Philadelphia, Pa.), 2014, 7, 1, 86-96; and Narayanapillai S C, et al., *Carcinogenesis*, 2014, 35, 10, 2365-72). On the other hand, dihydromethysticin has been reported to activate aryl hydrocarbon receptors that could introduce unwanted biological consequences (Li Y, et al., *Toxicological Sciences: an official journal of the Society of Toxicology*, 2011, 124, 2, 388-99).

In spite of the above reports there is currently a need for additional agents that are useful for treating or preventing cancer. In particular, there is a need for agents that have fewer side effects than (+)-Dihydromethysticin.

SUMMARY OF THE INVENTION

Certain embodiments of the invention provide a compound of formula (I):

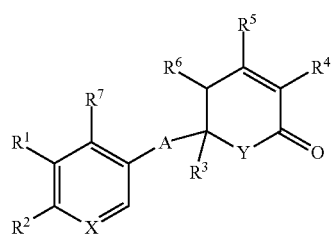

wherein:
$R^1$ is H, hydroxy, halo, trifluoromethyl, or $(C_1-C_6)$alkoxy;
$R^2$ is H, hydroxy, halo, trifluoromethyl, or $(C_1-C_6)$alkoxy;
and $R^7$ is H; or $R^7$ is H; and $R^1$ and $R^2$ taken together with the atoms to which they are attached form a 5-membered or 6-membered, saturated, partially unsaturated, or aromatic ring that comprises at least two carbon atoms and optionally comprises one or two heteroatoms selected from N, S, and O, which ring is optionally substituted with 1, 2, or 3 groups independently selected from halo, hydroxy, cyano, trifluoromethyl, trifluoromethoxy, $(C_1-C_3)$alkyl, and $(C_1-C_3)$alkoxy; or $R^2$ is H, hydroxy, halo, trifluoromethyl, or $(C_1-C_6)$alkoxy; and $R^1$ and $R^7$ taken together with the atoms to which they are attached form a benzo ring that is optionally substituted with 1, 2, or 3 groups independently selected from halo, hydroxy, cyano, trifluoromethyl, trifluoromethoxy, $(C_1-C_3)$alkyl, and $(C_1-C_3)$alkoxy;

X is $CR^a$ or N;
A is absent, $-CH_2-$, $-CH_2CH_2-$, $-CR^b=CH-$, or $-CH=CH-CH=CH-$;
$R^3$ is H, or $(C_1-C_6)$alkyl;
Y is O or $CH_2$;
$R^4$ is H, halo, $(C_1-C_6)$alkyl, or $(C_1-C_6)$alkoxy;
$R^5$ is H, halo, hydroxy, $(C_1-C_6)$alkyl, or $(C_1-C_6)$alkoxy that is optionally substituted with phenyl;
$R^6$ is H, halo, $(C_1-C_6)$alkyl, or $(C_1-C_6)$alkoxy;
$R^a$ is H, $(C_1-C_6)$alkyl, or $(C_1-C_6)$alkoxy; and
$R^b$ is H or phenyl that is optionally substituted with 1, 2, or 3 groups independently selected from halo, hydroxy, cyano, trifluoromethyl, trifluoromethoxy, $(C_1-C_3)$alkyl, and $(C_1-C_3)$alkoxy;

or a salt thereof;
provided the compound of formula (I) is not:

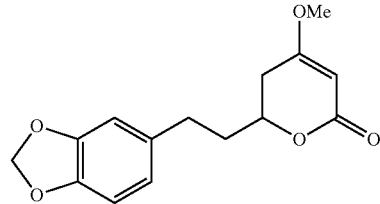

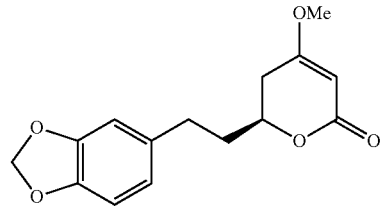

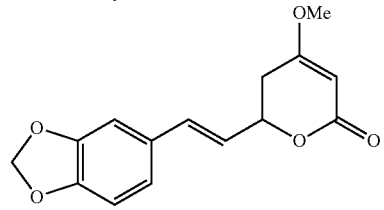

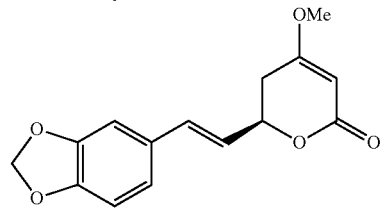

-continued

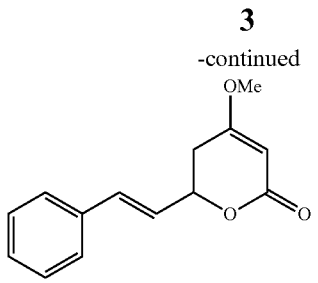

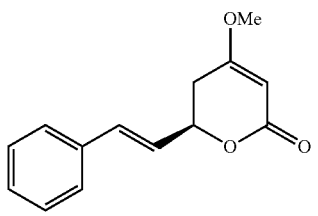

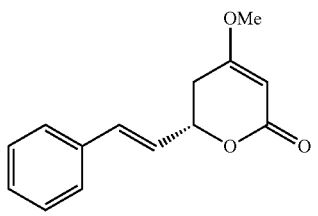

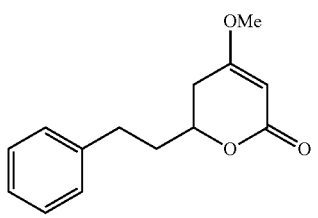

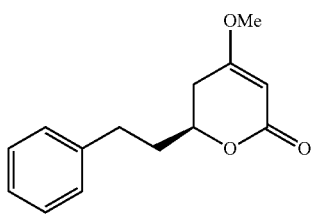

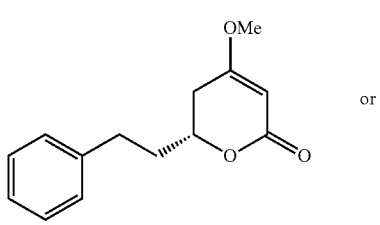

or

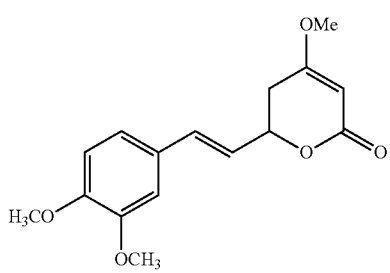

-continued

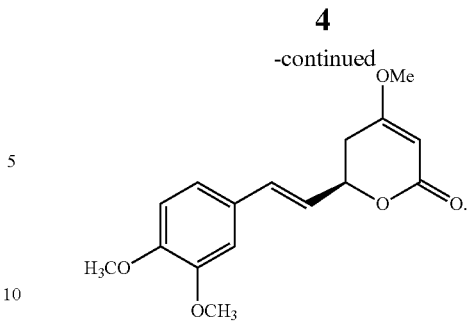

DETAILED DESCRIPTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$) alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. As described in the Examples, the compositions and compounds described herein, have chemopreventive properties, and therefore, are useful for both the treatment and prevention of cancer.

The terms "cancer" and "cancerous" refer to or describe the physiological condition in mammals that is typically characterized by unregulated cell accumulation. A "tumor" comprises one or more cancerous cells. Examples of cancer include, but are not limited to, carcinoma, lymphoma, blastoma, sarcoma, and leukemia or lymphoid malignancies. Specific examples of cancers include, but are not limited to, lung cancer, prostate cancer, skin cancer, melanoma, genitourinary cancer, colon and rectum cancer, breast cancer, ovary cancer, esophagial cancer, pancreatic cancer, urinary bladder cancer, cervical cancer, liver cancer, kidney and renal cancer, head and neck cancer, brain cancer or various hematological cancers.

Examples of cancer also include, but are not limited to, cancerous lesions in the above tissues, such as familial adenomatous polyposis, hyperplasia, dysplasia, aberrant crypt foci, adenoma, and others.

The phrase "detoxifying physical or chemical carcinogens" refers to enhancing elimination/deactivation of toxic species generated from physical or chemical carcinogens, reducing the generation of toxic species from physical or chemical carcinogens, and/or activating the immune system to improve self-defense against physical or chemical carcinogens.

As used herein, the terms "protein damage" refers to natural proteins, such as hemoglobin, being modified by the reactive metabolites/species generated by the chemical or physical carcinogens (Murphy et al., Chemico-Biological Interactions 1997; 103:153-166). Methods for measuring protein damage are known in the art, for example, as described in Murphy et al., Chemico-Biological Interactions 1997; 103:153-166.

As used herein, the term "mammal" includes, but is not limited to, humans, mice, rats, guinea pigs, monkeys, dogs, cats, horses, cows, pigs, and sheep, and poultry.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one embodiment the compound of formula (I) is a compound of formula (Ia):

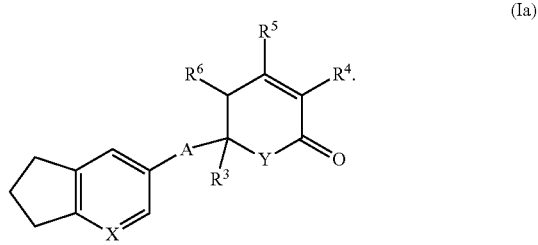

(Ia)

In one embodiment the compound of formula (I) is a compound of formula (Ib):

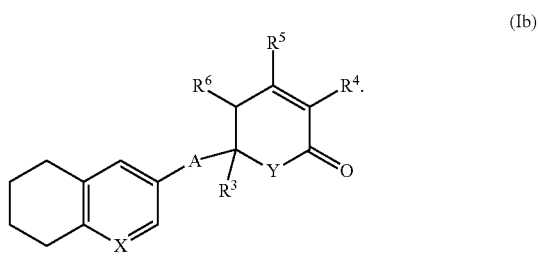

(Ib)

In one embodiment the compound of formula (I) is a compound of formula (Ic):

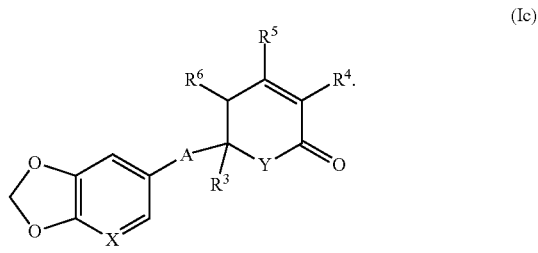

(Ic)

In one embodiment the compound of formula (I) is a compound of (Id):

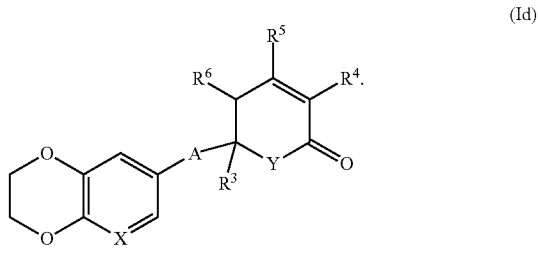

(Id)

In one embodiment the compound of formula (I) is a compound of formula (Ie):

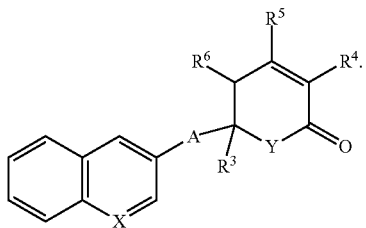

(Ie)

In one embodiment the compound of formula (I) is a compound of formula (If)

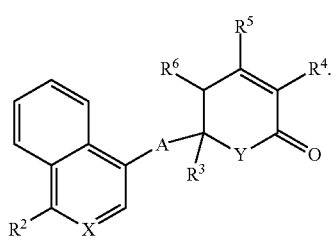

(If)

In one embodiment X is CH.
In one embodiment X is N.
In one embodiment A is absent.
In one embodiment A is CH$_2$.
In one embodiment A is —CH$_2$CH$_2$—.
In one embodiment A is —CH=CH—CH=CH—.
In one embodiment R$^3$ is H.
In one embodiment R$^3$ is methyl.
In one embodiment Y is O.
In one embodiment Y is CH$_2$.
In one embodiment R$^4$ is H or methyl.
In one embodiment R$^5$ is H, hydroxy, methoxy, ethoxy, propoxy, benzyloxy, or butoxy.
In one embodiment R$^6$ is H or methyl.
In one embodiment the compound is selected from:

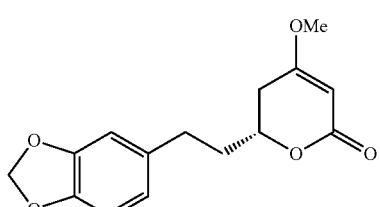

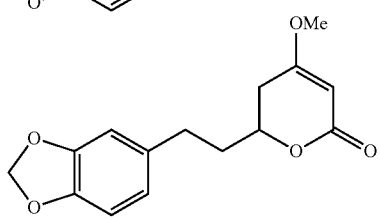

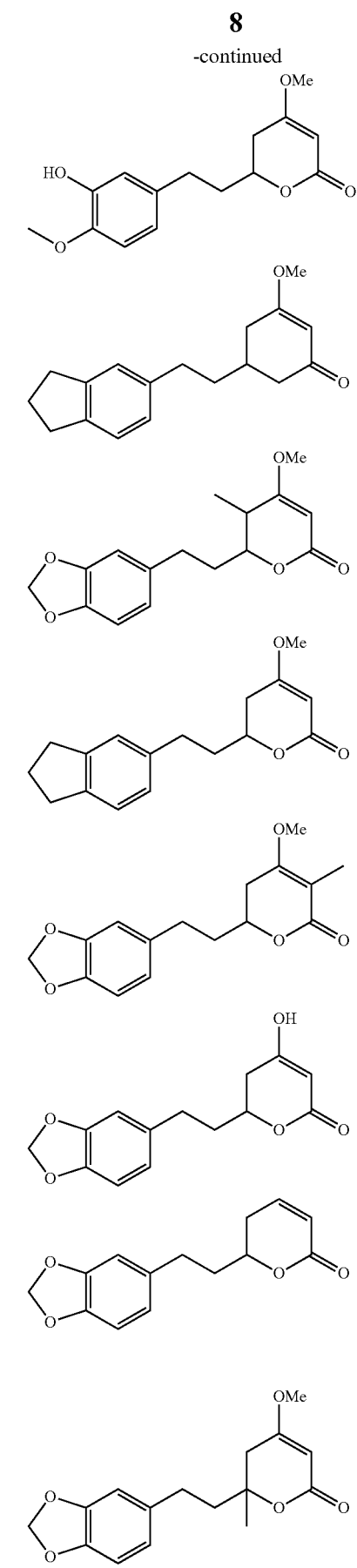

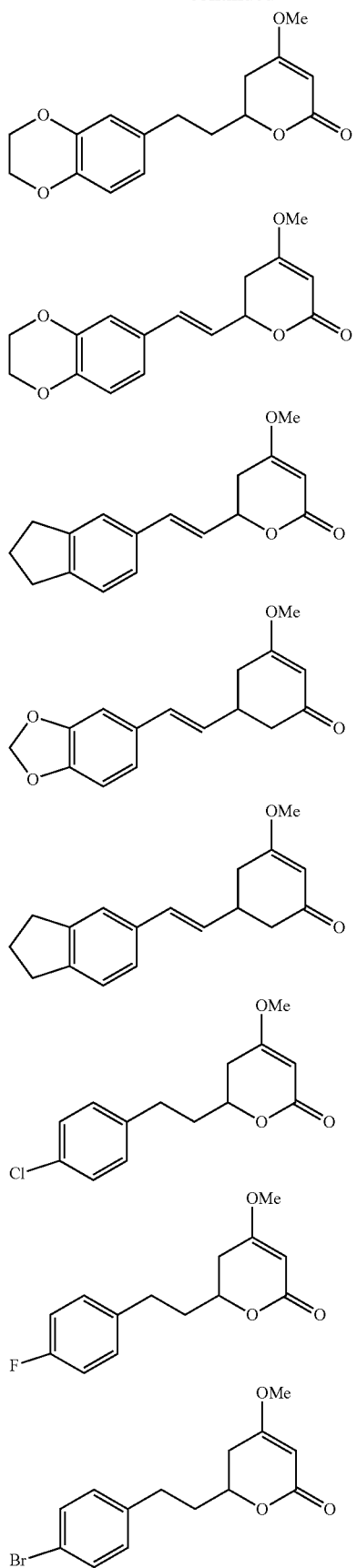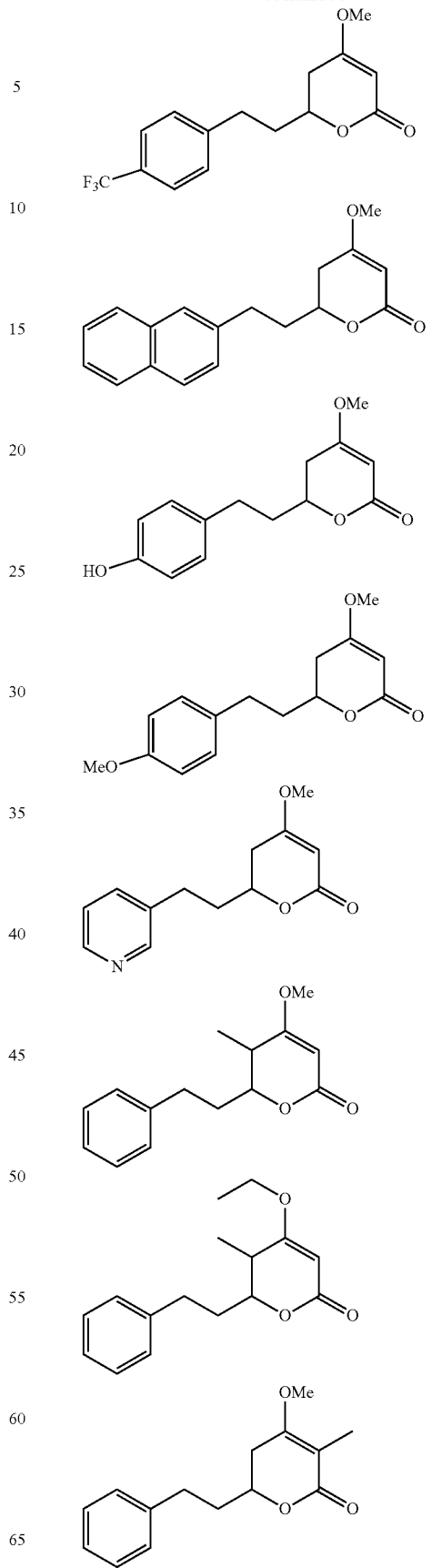

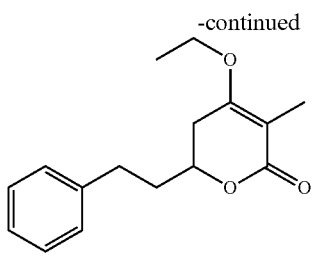
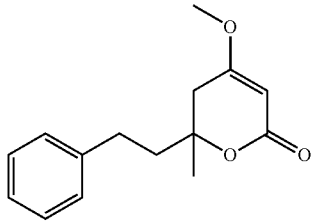
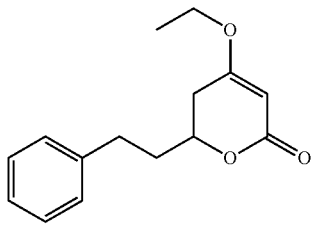
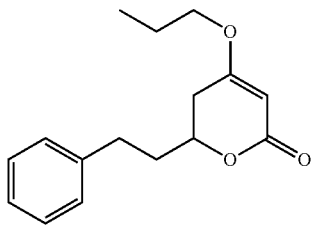
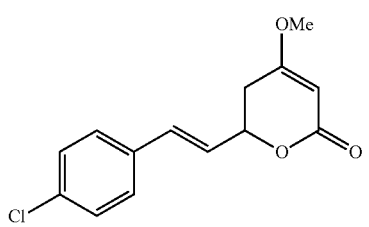
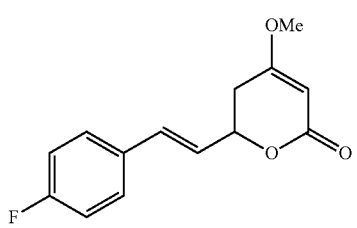
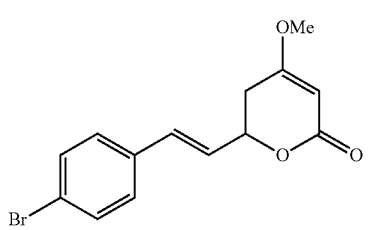
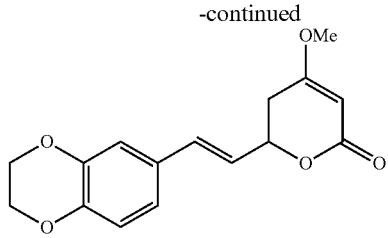
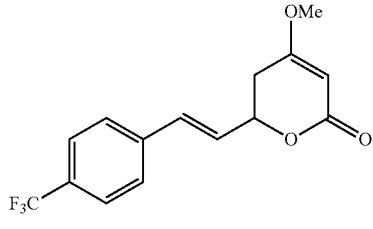
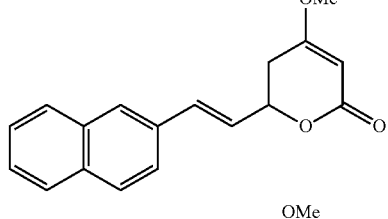
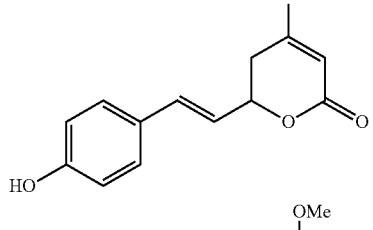
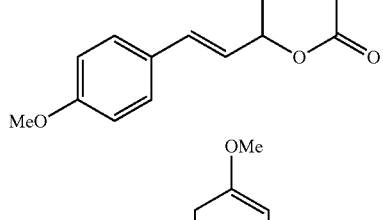
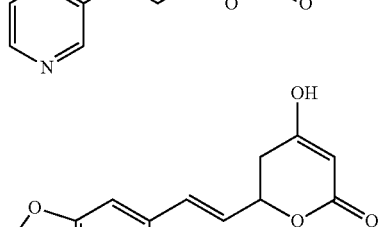
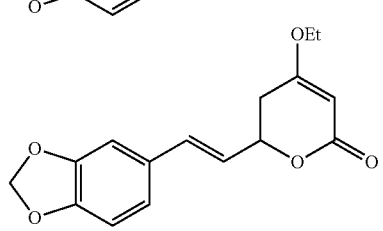

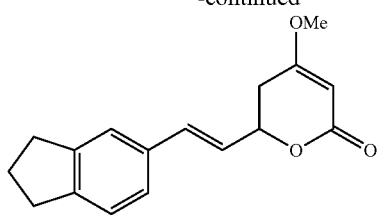
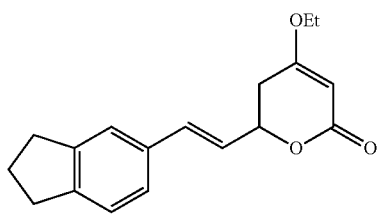
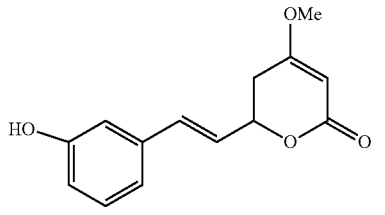
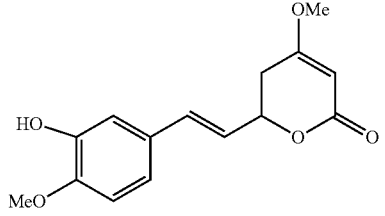
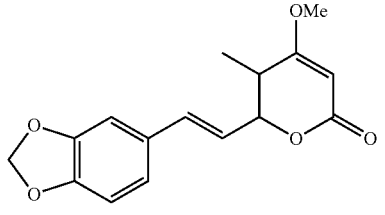
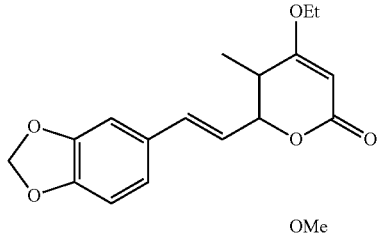
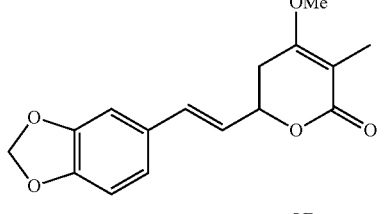
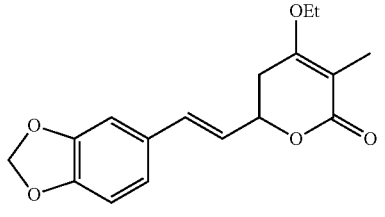
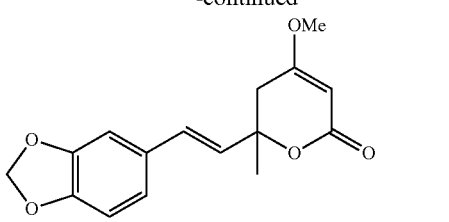
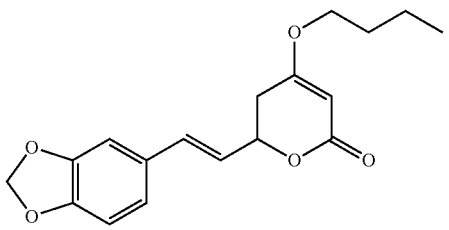
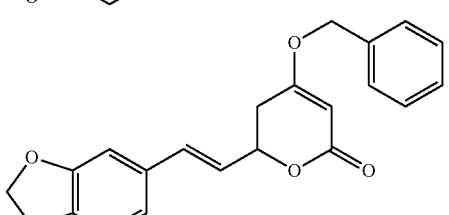
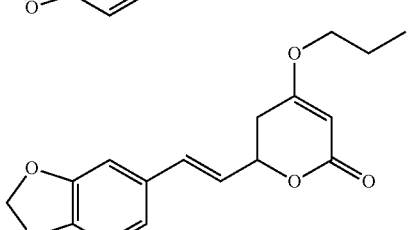
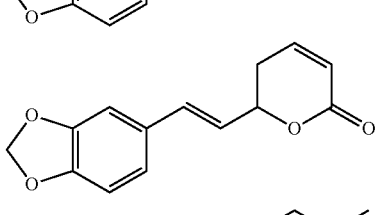
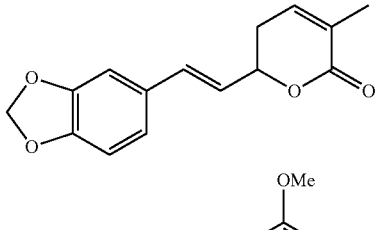
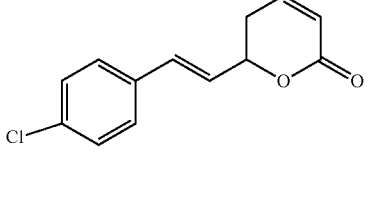
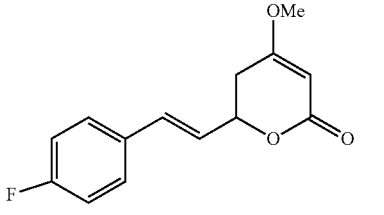

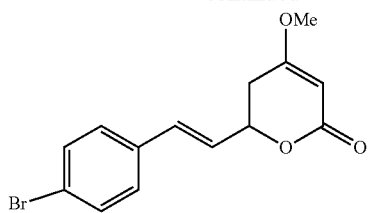
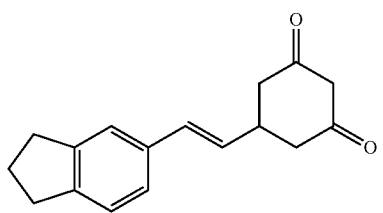
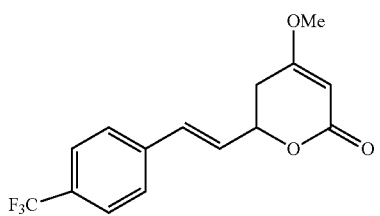
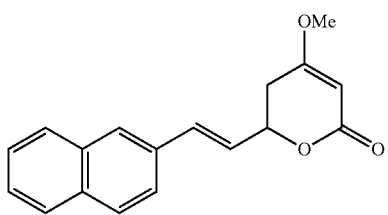
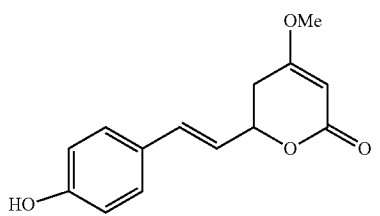
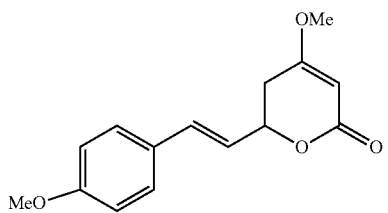
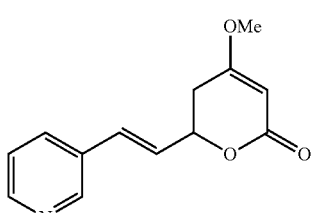
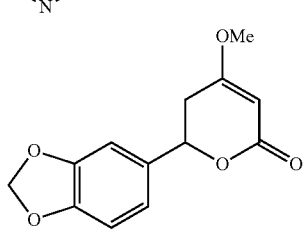
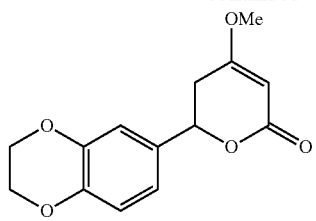
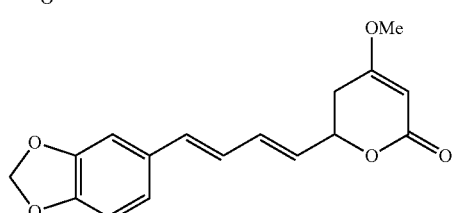
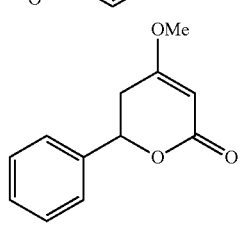
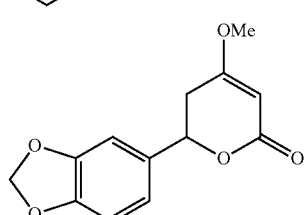
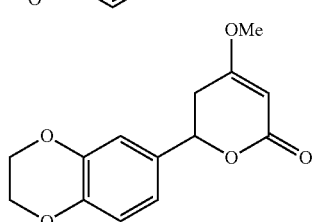
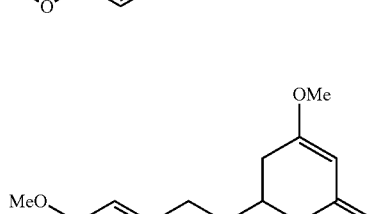
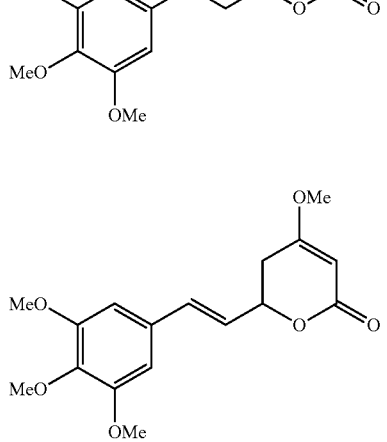

-continued

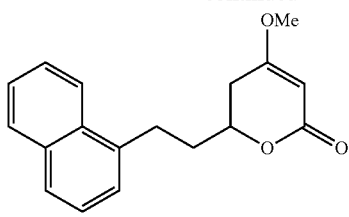

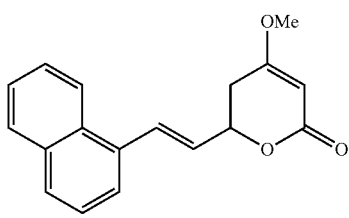

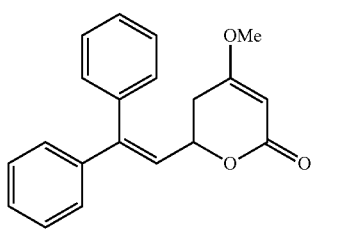

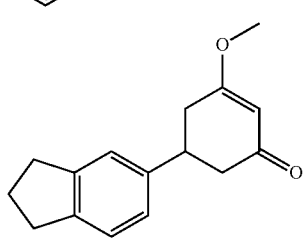

and salts thereof.

In one embodiment the compound is selected from:

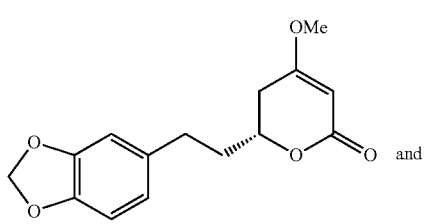 and

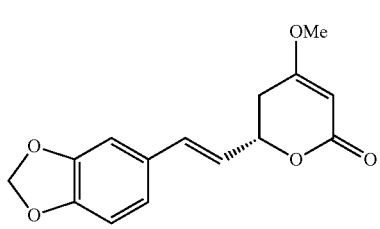

and salts thereof, wherein the compound is at least 51% the absolute stereoisomer depicted.

In one embodiment the compound is not:

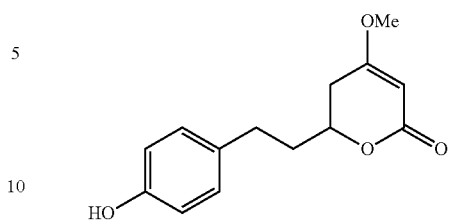

or a salt thereof.

In one embodiment the compound is not:

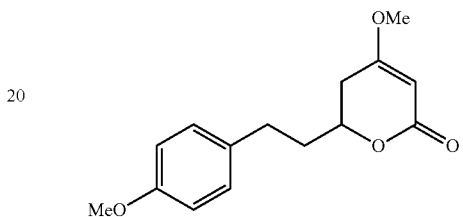

or a salt thereof.

In one embodiment the compound is not:

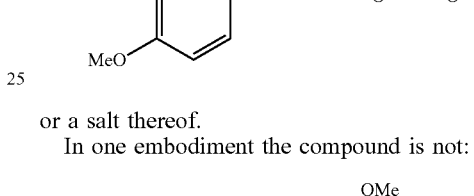

or a salt thereof.

In one embodiment the compound is not:

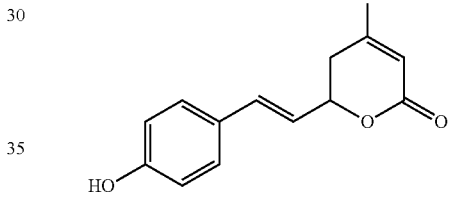

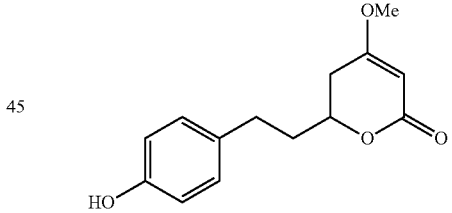

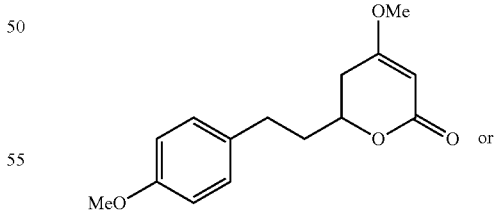 or

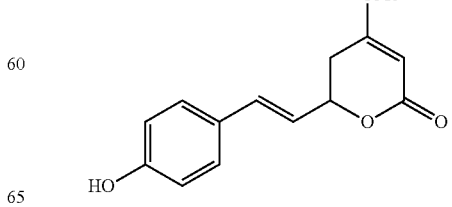

or a salt thereof.

Certain embodiments of the invention provide a compound of the invention for the prophylactic or therapeutic treatment of cancer in a mammal.

Certain embodiments of the invention provide the use of a compound of the invention to prepare a medicament for treating or preventing cancer in a mammal.

Certain embodiments of the invention provide a compound of the invention for use in medical therapy.

In certain embodiments, the cancer is lung cancer, prostate cancer, skin cancer, melanoma, genitourinary cancer, colon and rectum cancer, breast cancer, ovarian cancer, esophagial cancer, pancreatic cancer, urinary bladder cancer, cervical cancer, liver cancer, kidney and renal cancer, head and neck cancer, brain cancer or various hematological cancers.

Certain embodiments of the invention provide a method for preventing tumorigenesis, reducing DNA damage, reducing protein damage and/or detoxifying physical or chemical carcinogens in a mammal in need of such treatment comprising, administering to the mammal a compound of the invention.

In certain embodiments, the DNA damage is reduced by about 1%, 5%, 10%, 15%, 20%, 25%, 30%, 35%, 40%, 45%, 50%, 55%, 60%, 65%, 70%, 75%, 80%, 85%, 90%, 95%, or 100%, as compared to a mammal not administered a compound as described herein.

In certain embodiments, the protein damage is reduced by about 1%, 5%, 10%, 15%, 20%, 25%, 30%, 35%, 40%, 45%, 50%, 55%, 60%, 65%, 70%, 75%, 80%, 85%, 90%, 95%, or 100%, as compared to a mammal not administered a compound as described herein.

In certain embodiments, the DNA damage is a DNA adduct, caused by physical or chemical carcinogens.

In certain embodiments, the DNA adduct is a $O^6$-methylguanine DNA adduct.

In certain embodiments, the DNA adduct is a 7-methylguanine DNA adduct.

In certain embodiments, the DNA adducts are BaP, PhIP, POB and/or PHB adducts.

In certain embodiments, the DNA adducts are POB and PHB DNA adducts (e.g., 7-pobG, 7-[4-(3-pyridyl)-4-oxobut-1-yl]guanine; $O^2$-pobdT, $O^2$-[4-(3-pyridyl)-4-oxobut-1yl]thymidine; $O^6$-pobdG, $O^6$-[4-(3-pyridyl)-4-oxobut-1-yl]-2'-deoxyguanosine; $O^2$-pobC, $O^2$-[4-(3-pyridyl)-4-oxobut-1-yl]cytidine).

In cases where compounds are sufficiently basic or acidic, a salt of a compound of formula I can be useful as an intermediate for isolating or purifying a compound of formula I.

Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect NNK-induced $O^6$-mG in A/J mouse lung tissues may be determined using pharmacological models which are well known to the art, or using Test A described below.

Test A.
General Procedure of the In Vivo Effect on NNK-induced $O^6$-mG in A/J Mouse Lung Tissues Five-six week old A/J mice were purchased from Jackson Lab. After one week of acclimatization, mice were randomized into different groups. Mice were given to the AIN-G powdered diet supplemented with the corresponding compound at a dose of 0.2 mg/g of diet for seven days. Subsequently, with the exception of mice in the negative control groups, animals were given NNK (100 mg/kg of bodyweight at the beginning of Day 7 via i.p. injection) (control mice will be given saline). Four hours NNK administration, mice in each group were euthanized with serum, urine, lung and liver tissues collected. $O^6$-mG DNA adducts in the lung tissues were quantified following established procedures (1, 2). The relative amount of reduction was calculated as the percentage of reduction relative the amount of $O^6$-mG in the NNK-treated positive control group.

The ability of a compound of the invention to effect CYP1A1 activation may be determined using pharmacological models which are well known to the art, or using Test B described below.

Test B.
General Procedures of the In Vitro Effect on CYP1A1 Activation

Hepe1c1c7 cells were cultured under standard conditions and seeded in 6-well plate. After complete attachment (12-24 hours after seeding), the cells were treated with the corresponding compounds at the concentration of 5 μM, supplemented in 0.5% DMSO. Cells were trypsinized and pelleted. mRNAs were isolated. The relative amount of CYP1A1 mRNA were quantified via q-RT PCR and normalized to the amount of GAPDH mRNA from the same sample. Induction of CYP1A1 mRNA is defined as the ratio of CYP1A1 mRNA between treated samples to the untreated sample.

Data for representative compounds of the invention from Test A and Test B is provided in the following Table.

TABLE

| Compound | Relative amount of reduction in $O^6$-mG (mean ± SD) % in comparison to NNK-treated control | Induction of CYP1A1 mRNA |
|---|---|---|
| (structure) | 76.9 ± 2.6 | 1.88 ± 0.07 |

TABLE-continued

| Compound | Relative amount of reduction in $O^6$-mG (mean ± SD) % in comparison to NNK-treated control | Induction of CYP1A1 mRNA |
|---|---|---|
| [structure: methylenedioxyphenyl-ethyl-dihydropyranone with OMe] | 72.7 ± 6.6 | |
| [structure: methylenedioxyphenyl-ethyl-dihydropyranone with OMe, (S)-config] | 79.6 ± 1.5 | |
| [structure: methylenedioxyphenyl-vinyl-dihydropyranone with OMe] | 54.6 ± 1.2 | 0.26 ± 0.01 |
| [structure: methylenedioxyphenyl-ethyl-methoxycyclohexenone] | 63.7 ± 21.9 | 5.58 ± 0.55 |
| [structure: hydroxy-methoxyphenyl-ethyl-dihydropyranone with OMe] | −2.6 ± 14.7 | 5.61 ± 0.40 |
| [structure: indanyl-ethyl-methoxycyclohexenone] | 11.8 ± 23.1 | |

TABLE-continued
| Compound | Relative amount of reduction in $O^6$-mG (mean ± SD) % in comparison to NNK-treated control | Induction of CYP1A1 mRNA |
|---|---|---|
| 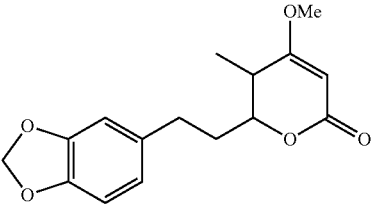 [SMILES: COC1=CC(=O)OC(CCc2ccc3c(c2)OCO3)C1C] | N/A | 2.16 ± 0.11 |
| 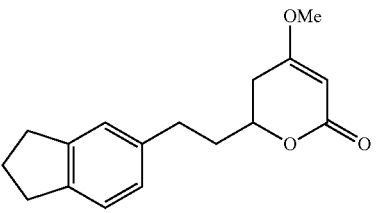 [SMILES: COC1=CC(=O)OC(CCc2ccc3c(c2)CCC3)C1] | 29.7 ± 16.3 | 0.79 ± 0.02 |
| 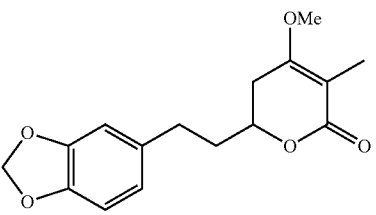 [SMILES: COC1=C(C)C(=O)OC(CCc2ccc3c(c2)OCO3)C1] | 65.3 ± 5.8 | 0.59 ± 0.04 |
| 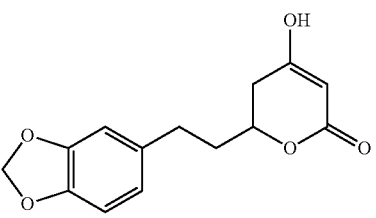 [SMILES: O=C1C=C(O)CC(CCc2ccc3c(c2)OCO3)O1] | 55.9 ± 19.7 | 1.20 ± 0.1 |
| 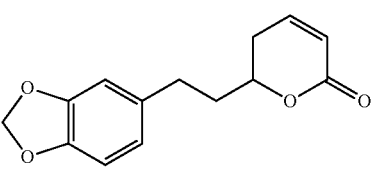 [SMILES: O=C1C=CCC(CCc2ccc3c(c2)OCO3)O1] | 35.2 ± 31.8 | 5.94 ± 0.22 |
| 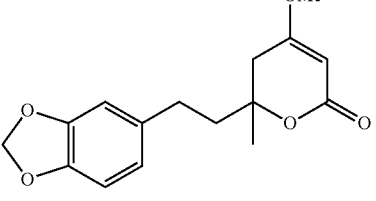 | 56.2 ± 8.1 | 2.49 ± 0.08 |
| 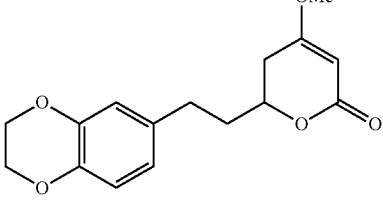 | 3.24 ± 13.4 | 3.73 ± 0.26 |

TABLE-continued

| Compound | Relative amount of reduction in $O^6$-mG (mean ± SD) % in comparison to NNK-treated control | Induction of CYP1A1 mRNA |
|---|---|---|
| (structure: 2,3-dihydrobenzo[b][1,4]dioxin-6-yl vinyl dihydropyranone with OMe) | 5.2 ± 13.0 | 1.15 ± 0.02 |
| (structure: indan-5-yl vinyl dihydropyranone with OMe) | | |
| (structure: benzo[d][1,3]dioxol-5-yl vinyl cyclohexenone with OMe) | | |
| (structure: indan-5-yl vinyl cyclohexenone with OMe) | | |
| (structure: 3,4,5-trimethoxyphenyl ethyl dihydropyranone with OMe) | | |
| (structure: 4-chlorophenyl ethyl dihydropyranone with OMe) | | |

TABLE-continued
| Compound | Relative amount of reduction in O$^6$-mG (mean ± SD) % in comparison to NNK-treated control | Induction of CYP1A1 mRNA |
|---|---|---|
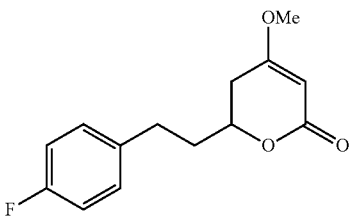
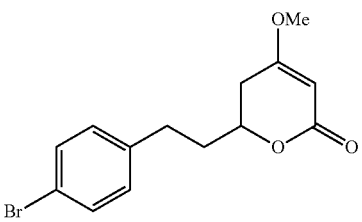 [SMILES: COC1=CC(=O)OC(CCc2ccc(Cl)cc2)C1]
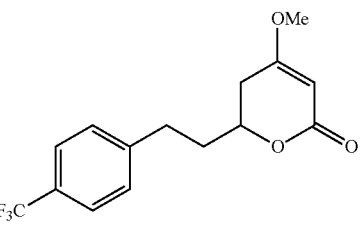
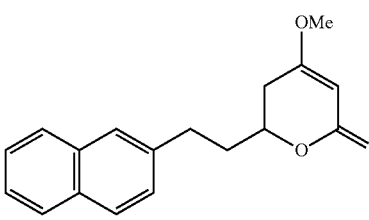
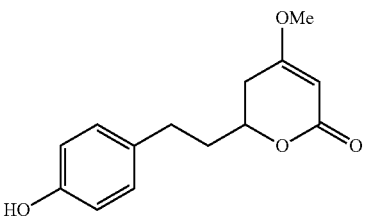 [SMILES: COC1=CC(=O)OC(CCc2ccc(O)cc2)C1]
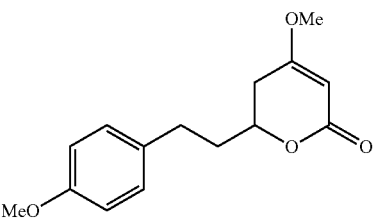 [SMILES: COC1=CC(=O)OC(CCc2ccc(OC)cc2)C1]

TABLE-continued

| Compound | Relative amount of reduction in $O^6$-mG (mean ± SD) % in comparison to NNK-treated control | Induction of CYP1A1 mRNA |
|---|---|---|

TABLE-continued

| Compound | Relative amount of reduction in O⁶-mG (mean ± SD) % in comparison to NNK-treated control | Induction of CYP1A1 mRNA |
|---|---|---|

TABLE-continued

| Compound | Relative amount of reduction in $O^6$-mG (mean ± SD) % in comparison to NNK-treated control | Induction of CYP1A1 mRNA |
|---|---|---|
| 4-Br-phenyl styryl dihydropyranone (OMe) | | |
| benzodioxine styryl dihydropyranone (OMe) | 5.2 ± 13.0 | 1.15 ± 0.02 |
| 4-CF₃-phenyl styryl dihydropyranone (OMe) | | |
| 2-naphthyl styryl dihydropyranone (OMe) | | |
| 4-HO-phenyl styryl dihydropyranone (OMe) | | |
| 4-MeO-phenyl styryl dihydropyranone (OMe) | | |

TABLE-continued

| Compound | Relative amount of reduction in O⁶-mG (mean ± SD) % in comparison to NNK-treated control | Induction of CYP1A1 mRNA |
| --- | --- | --- |

TABLE-continued
| Compound | Relative amount of reduction in $O^6$-mG (mean ± SD) % in comparison to NNK-treated control | Induction of CYP1A1 mRNA |
|---|---|---|
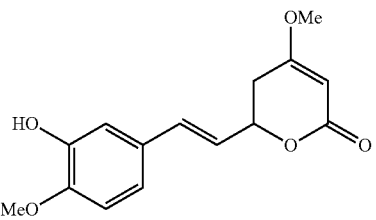 [SMILES: COC1=CC(=O)OC(/C=C/c2ccc(OC)c(O)c2)C1]
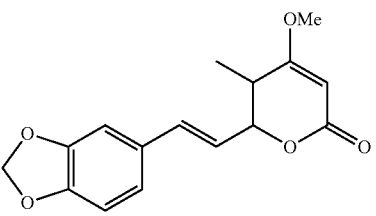 [SMILES: COC1=CC(=O)OC(/C=C/c2ccc3c(c2)OCO3)C1C]
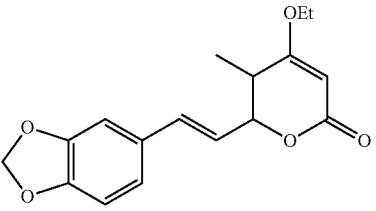 [SMILES: CCOC1=CC(=O)OC(/C=C/c2ccc3c(c2)OCO3)C1C]
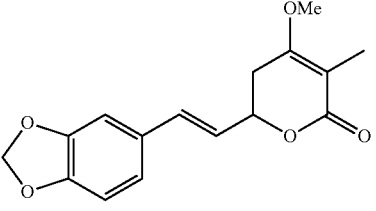 [SMILES: COC1=C(C)C(=O)OC(/C=C/c2ccc3c(c2)OCO3)C1]
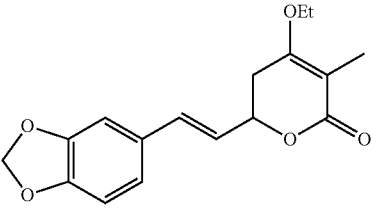 [SMILES: CCOC1=C(C)C(=O)OC(/C=C/c2ccc3c(c2)OCO3)C1]
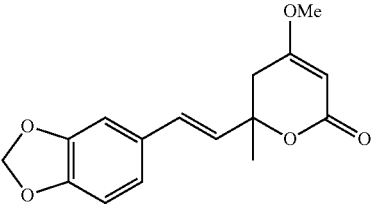 [SMILES: COC1=CC(=O)OC(C)(/C=C/c2ccc3c(c2)OCO3)C1]

TABLE-continued

| Compound | Relative amount of reduction in O$^6$-mG (mean ± SD) % in comparison to NNK-treated control | Induction of CYP1A1 mRNA |
|---|---|---|

TABLE-continued
| Compound | Relative amount of reduction in O⁶-mG (mean ± SD) % in comparison to NNK-treated control | Induction of CYP1A1 mRNA |
|---|---|---|
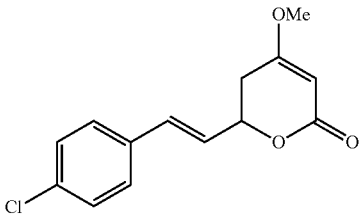 [SMILES: COC1=CC(=O)OC(/C=C/c2ccc(Cl)cc2)C1]
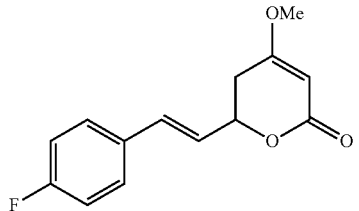 [SMILES: COC1=CC(=O)OC(/C=C/c2ccc(F)cc2)C1]
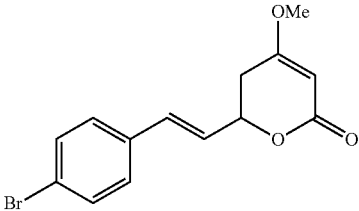
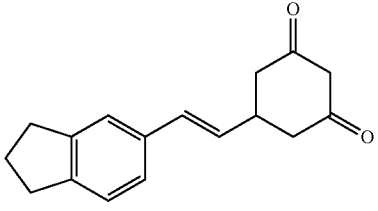 [SMILES: O=C1CC(=O)CC(/C=C/c2ccc3c(c2)CCC3)C1]
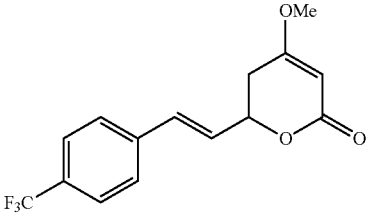 [SMILES: COC1=CC(=O)OC(/C=C/c2ccc(C(F)(F)F)cc2)C1]
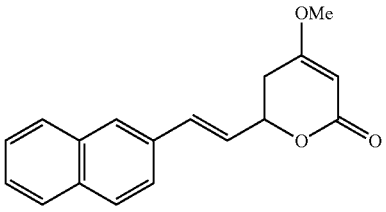 [SMILES: COC1=CC(=O)OC(/C=C/c2ccc3ccccc3c2)C1]

TABLE-continued

| Compound | Relative amount of reduction in $O^6$-mG (mean ± SD) % in comparison to NNK-treated control | Induction of CYP1A1 mRNA |
|---|---|---|

(Structures shown, from top to bottom:)

- 6-[(E)-2-(4-hydroxyphenyl)vinyl]-4-methoxy-5,6-dihydro-2H-pyran-2-one
- 6-[(E)-2-(4-methoxyphenyl)vinyl]-4-methoxy-5,6-dihydro-2H-pyran-2-one
- 4-methoxy-6-[(E)-2-(pyridin-3-yl)vinyl]-5,6-dihydro-2H-pyran-2-one
- 6-(1,3-benzodioxol-5-yl)-4-methoxy-5,6-dihydro-2H-pyran-2-one
- 6-(2,3-dihydro-1,4-benzodioxin-6-yl)-4-methoxy-5,6-dihydro-2H-pyran-2-one
- 6-[(1E,3E)-4-(1,3-benzodioxol-5-yl)buta-1,3-dien-1-yl]-4-methoxy-5,6-dihydro-2H-pyran-2-one
- 4-methoxy-6-phenyl-5,6-dihydro-2H-pyran-2-one The invention will now be illustrated by the following non-limiting Examples.

EXAMPLES

General Procedure of the Synthesis and Characterization

Experimental Section

Chemistry: All commercial reagents and anhydrous solvents were purchased from vendors and were used without further purification or distillation, unless otherwise stated. All non-aqueous reactions were carried out under an atmosphere of dry nitrogen in dried glassware. Analytical thin layer chromatography (TLC) was performed on EM Science silica gel 60 $F_{254}$ (0.25 mm). Compounds were visualized by UV light and further stained with p-anisaldehyde solutions followed by heating. Flash column chromatography was performed on Whatman Inc. silica gel (230-400 mesh). The $^1$H NMR, $^{13}$C NMR spectra were recorded on a Bruker Avance 400 MHz spectrometer. The chemical shifts for $^1$H NMR are reported in ppm downfield to $CDCl_3$ (7.26 ppm), coupling constants were in Hz. ESI mode mass spectra were recorded on a Bruker BiotofII mass spectrometer.

Preparation of Compound 104:

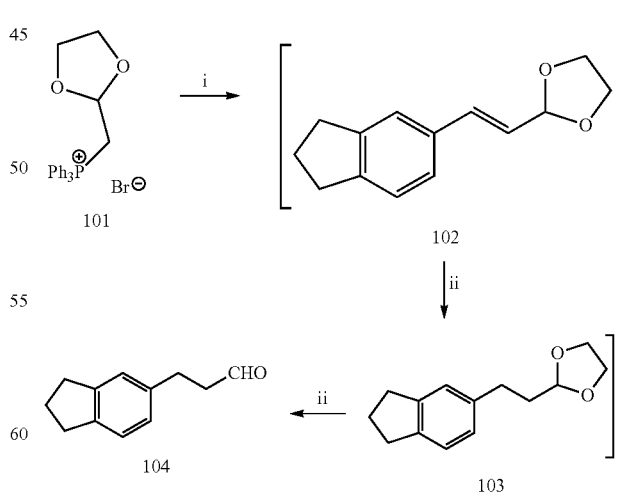

Reagents and conditions: (i) LiOMe, dry THF, 0° C., Indane aldehyde, 70° C., 6 h; (ii) $H_2$, Pd/C (1 atm), THF, 2 h; (iii) dil. HCl, THF, RT, 2 h, 50% over three steps.

Lithium methoxide (9.9 mmol) in methanol (5 mL) was added dropwise to a stirred solution of (1,3-dioxolan-2-yl) methyl triphenylphosphonium bromide 101 (9.9 mmol) in dry THF (15 mL) under nitrogen atmosphere at 0° C. and stirred at room temperature for 30 min. Indane aldehyde (6.6 mmol) in dry THF (5 mL) was added dropwise to the reaction mixture at the same temperature and stirred for another 30 min. The reaction mixture was stirred at 70° C. for 6 h and after completion of reaction was quenched by the addition of saturated $NH_4Cl$ (5 mL) at 0° C. The compound was extracted from aqueous layer using EtOAC (2×10 mL). The combined organic layers were dried over $MgSO_4$, and the solvent was evaporated in vacuo to afford the crude product, which was purified by column chromatography using EtOAc in Hexanes (10-15% EA in Hx) as gradient eluents to afford the olefinic acetal 102. Thus obtained olefinic acetal 102 in THF (15 mL) was subjected to hydrogenation, using Pd/C (5% wt) under $H_2$ atmosphere. The flask was degassed under high vacuum and the reaction was carried out under $H_2$ atmosphere at 1 atm pressure ($H_2$ balloon) for 2 h. After completion, was filtered through the celite bed and to thus obtained solution was added 1N HCl (20 mL) at 0-5° C. After stirring the reaction mixture at room temperature for 2 hours, THF was removed under reduced pressure and was diluted with EtOAc and extracted with EtOAc (2×10 mL). The combined organic layers were washed with saturated $NaHCO_3$ solution (2×10 mL) and dried over anhydrous $MgSO_4$. The solvent was evaporated in vacuo and the residue was dried under high vacuum for 2 hours, to yield the compound 104, (592 mg, 50% yield) as light yellow oil, which was taken to the next step without purification. TLC (EtOAc:Hexane=1:9) Rf 0.35. $^1H$ NMR (500 MHz, $CDCl_3$): δ 9.80 (s, 1H), 7.13 (d, J=7.5 Hz, 1H), 7.05 (s, 1H), 6.95 (d, J=8.0 Hz, 1H), 2.91 (t, J=7.5 Hz, 2H), 2.88-2.84 (m, 4H), 2.74 (t, J=7.5 Hz, 2H), 2.05 (quint, J=7.5 Hz, 2H); $^{13}C$ NMR (125 MHz, $CDCl_3$) δ 201.8, 144.7, 142.2, 138.1, 126.0, 124.4, 124.3, 45.6, 32.7, 32.4, 28.0, 25.5; ESI-MS (positive): m/z 175.1.

Example 1

Synthesis of Compound 9

Reagents and conditions:(i) (a) NaH, BuLi, dry THF, 0° C., 30 min, (b) compound 104, −55° C. to RT, 6 h; (ii) (a) $K_2CO_3$, MeOH, RT, 6 h, (b) Dimethyl sulfate, acetone, RT, 12 h, 64%.

The synthesis of Compound 9 was achieved in two step procedure. In the first step, ethylacetoacetate (2.29 mmol) was added drop wise to slurry of sodium hydride (4.35 mmol) in dry THF (10 mL) under nitrogen atmosphere at 0° C. and stirred at same temperature for 30 min. Then n-BuLi (4.35 mmol) was added drop wise over a period of 10 min and further stirred for another 30 min at 0° C. The reaction mixture was brought to −55° C., and compound 104 (2.29 mmol) in dry THF (5 mL) was added dropwise. After 30 min, reaction temperature was brought to room temperature and stirred for 6 hours. Upon completion, reaction mixture was quenched by the addition of saturated $NH_4Cl$ (5 mL), the compound was extracted with ethyl acetate (2×5 mL). Organic layers were combined, dried over anhydrous $MgSO_4$. The solvent was evaporated in vacuo to give aldol adduct δ-hydroxy-β-ketoester 105.

In second step, anhydrous $K_2CO_3$ (4.58 mml) was added to aldol adduct δ-hydroxy-β-ketoester 105 in methanol (10 mL) at room temperature and stirred for 6 hours. Upon reaction completion, methanol was removed under reduced pressure and the reaction mass was redissolved in anhydrous acetone (10 mL) and dimethylsulfate (4.58 mmol) was added, the reaction mixture was stirred at room temperature for 12 h. The solvent was removed under reduced pressure and diluted with ethyl acetate (10 mL) and water (10 mL) followed by EtOAc extraction (2×5 mL). The combined organic layers were dried over anhydrous $MgSO_4$. Ethyl acetate was evaporated in vacuo and the residue was purified by column chromatography on silica gel using EtOAc in Hexanes (30-50% EA in Hx) as solvent gradient to give pure compound 1 (400 mg, 64%) as a light yellow solid. TLC (EtOAc:Hexane=3:7) Rf 0.32, HPLC purity 99.5%, $^1H$ NMR (500 MHz, $CDCl_3$): δ 7.13 (d, J=7.5 Hz, 1H), 7.07 (s, 1H), 6.96 (d, J=7.5 Hz, 1H), 5.13 (d, J=1 Hz, 1H), 4.39-4.33 (s, 1H), 3.71 (s, 3H), 2.88-2.80 (m, 5H), 2.76-2.49 (m, 1H), 2.32-2.28 (m, 1H), 2.13 (dd, J=8.5, 6.0 Hz, 1H), 2.13-2.07 (m, 1H), 1.93-1.86 (m, 1H); $^{13}C$ NMR (125 MHz, $CDCl_3$)

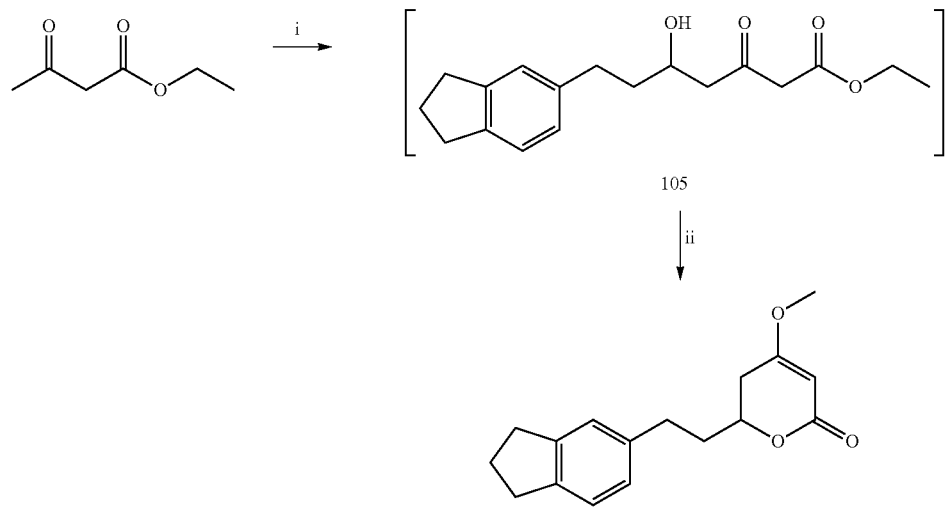

Compound 9

δ 172.7, 167.3, 144.6, 142.0, 138.6, 126.2, 124.4, 124.3, 90.3, 74.8, 55.9, 36.6, 33.0, 32.7, 32.4, 30.7, 25.4; ESI-MS (positive): m/z 273.2.

Preparation of Compound 108:

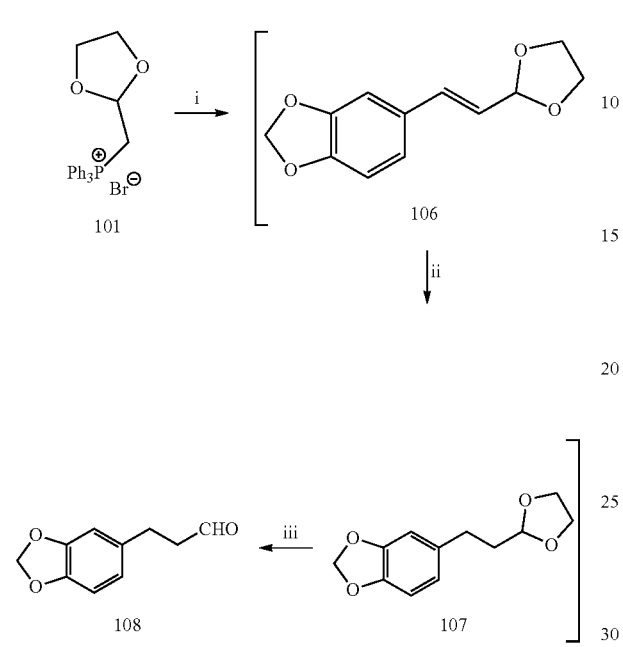

Reagents and conditions:(i) LiOMe, dry THF, 0° C., Piperonal, 70° C., 6 h; (ii) H$_2$, Pd/C (1 atm), THF, 2 h; (iii) dil. HCl, THF, RT, 2 h, 52% over three steps.

By following the similar synthetic sequence the aldehyde 108 was achieved in 52% overall yield as a light yellow oil. The spectral data were in complete agreement with the literature values. TLC (EtOAc:Hexane=1:9) Rf0.31. $^1$H NMR (500 MHz, CDCl$_3$): δ 6.73 (d, J=7.5 Hz, 1H), 6.64 (s, 1H), 6.63 (d, J=1.5 Hz, 1H), 5.91 (s, 2H), 2.87 (t, J=7.5 Hz, 2H), 2.74 (J=7.5 Hz, 2H); $^{13}$C NMR (125 MHz, CDCl$_3$) δ 201.5, 147.7, 146.0, 134.1, 121.0, 108.7, 108.3, 100.9, 45.5, 27.9. ESI-MS (positive): m/z 179.0.

Example 2

Synthesis of Compound 5

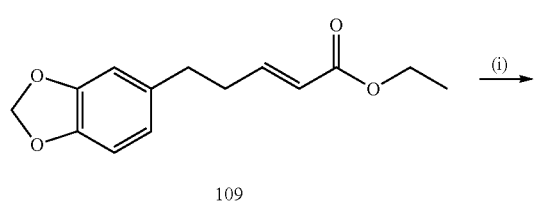

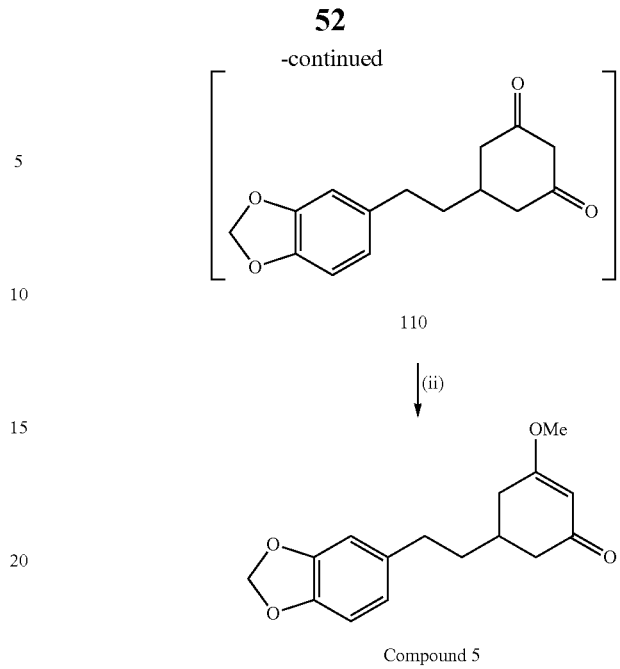

Reagents and conditions:(i) NaH, THF:Toluene (1:1), acetone, 0° C.-RT, 4 h, Dil. HCl, 25% (ii) Dimethyl sulfate, acetone, RT, 12 h, 84%.

To a stirred solution of 1:1 mixture of dry THF and dry Toluene (15 mL) was added NaH (5.80 mmol) at room temperature under Nitrogen atmosphere. The reaction mixture was cooled to 0° C. and acetone (5.80 mmol) was added and stirred for 15 min at room temperature, followed by the olefin ester 109 (4.83 mmol) in dry THF (5 mL) was added. After completion of reaction (3 h) dil. HCl (5 mL) was added, layer separation was done, extracted the compound using EtOAc (3×15 mL). The combined organic layer was dried over anhydrous Na$_2$SO$_4$ and the solvent was evaporated under vacuo to afford the crude diketone 110, was redissolved in acetone (10 mL) was added K$_2$CO$_3$ (7.2 mmol) followed by dimethyl sulfate (7.2 mmol) at RT. The reaction mixture was allowed to stir for 12 h. The solvent was removed under reduced pressure and was diluted with EtOAc (10 mL) and distilled water (10 mL), layer separation was done, extracted the compound using EtOAc (3×15 mL). The combined organic layer was dried over anhydrous Na$_2$SO$_4$ and the solvent was evaporated under vacuo and the residue was purified by column chromatography on silica gel using EtOAc in Hexanes (30-50% EA in Hx) as solvent gradient to give pure compound Compound 5 (397 mg, 30%) as a light yellow solid. TLC (EtOAc:Hexane=3:7) Rf0.35, HPLC purity 98%, $^1$H NMR (500 MHz, CDCl$_3$): δ 6.72 (d, J=8.0 Hz, 1H), 6.65 (s, 1H), 6.61 (d, J=8.0 Hz, 1H), 5.91 (s, 2H), 5.35 (s, 1H), 3.68 (s, 3H), 2.59-2.51 (m, 2H), 2.48-2.47 (m, 2H), 2.22-2.17 (m, 1H), 2.11-2.07 (d, 2H), 1.70-1.65 (m, 2H); $^{13}$C NMR (125 MHz, CDCl$_3$) δ 199.3, 178.0, 147.7, 145.8, 135.4, 121.1, 108.7, 108.3, 102.2, 100.9, 55.8, 43.2, 37.4, 35.3, 33.0, 32.6; ESI-MS (positive): m/z 275.1.

Example 3

Synthesis of Compound 7

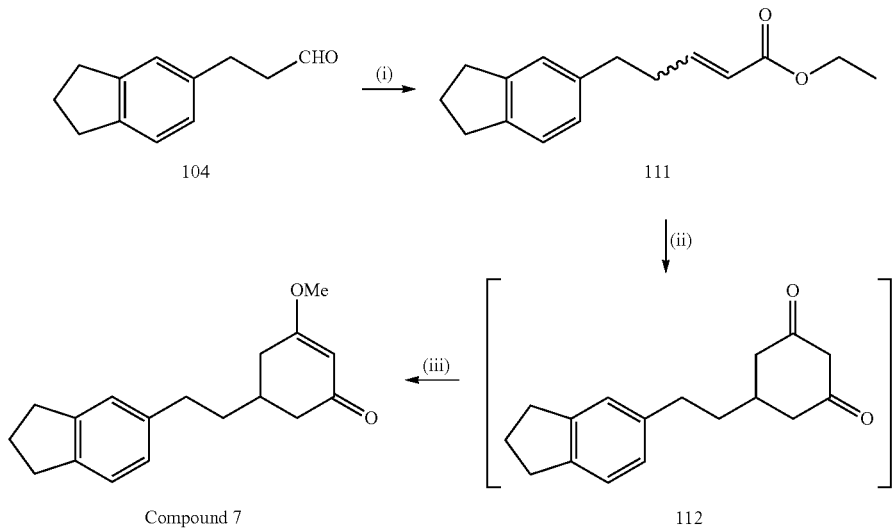

Reagents and conditions: (i) wittig ylide, THF, reflux, 12 h, 95% (ii) NaH, THF:Toluene (1:1), acetone, 0° C.-RT, 4 h, Dil. HCl, 25% based on trans olefin ester, (iii) Dimethyl sulfate, acetone, RT, 12 h, 84%.

To a stirred solution of aldehyde (3.44 mmol) was added dry THF (15 mL) followed by wittig ylide (4.13 mmol) at room temperature under Nitrogen atmosphere. Refluxed the reaction mixture for 12 h, after completion, the reaction mixture was adsorbed on silica gel and was purified using EtOAc in Hexanes (5-10% EA in Hexanes) as solvent gradient to give pure compound 111 (800 mg, 95%) as a light yellow solid. TLC (EtOAc:Hexane=1:9) Rf=0.4, obtained as 1.5:1 cis-trans olefinic ester mixture, $^1$H NMR (500 MHz, CDCl$_3$): δ 6.95 (d, J=22.5 Hz, 1H), 6.92 (s, 1H), 6.91-6.84 (m, 2H), 6.88-6.87 (m, 1H), 5.78 (d, J=16.0 Hz, 2H), 4.14-4.09 (m, 6H), 3.61 (t, J=6.0 Hz, 4H), 2.82-2.78 (m, 5H), 2.66 (t, J=7.5 Hz, 2H), 2.44 (q, J=8.0 Hz, 2H), 2.26-2.22 (m, 4H), 2.00-179 (m, 4H), 1.68-1.65 (m, 4H), 1.23-1.18 (m, 8H); $^{13}$C NMR (125 MHz, CDCl$_3$) δ 166.6, 148.3, 126.1, 124.33, 124.30, 121.7, 121.6, 62.0, 60.2, 34.2, 32.8, 32.4, 30.9, 28.4, 25.5, 14.2; ESI-MS (positive): m/z 246.1.

To a stirred solution of 1:1 mixture of dry THF and dry Toluene (10 mL) was added NaH (3.43 mmol) at room temperature under Nitrogen atmosphere. The reaction mixture was cooled to 0° C. and acetone (3.43 mmol) was added and stirred for 15 min at room temperature, followed by the olefin ester 111 in dry THF (5 mL) was added. After completion of reaction (3 h) dil. HCl was added, layer separation was done, extracted the compound using EtOAc (3×15 mL). The combined organic layer was dried over anhydrous Na$_2$SO$_4$ and the solvent was evaporated under vacuo to afford the crude diketone 112, to which acetone (5 mL) was added followed by K$_2$CO$_3$ (5.72 mmol) and dimethyl sulfate (5.72 mmol) were added at RT. The reaction mixture was allowed to stir for 12 h. The solvent was removed under reduced pressure and was diluted with EtOAc (5 mL) and distilled water (5 mL), layer separation was done, and the compound extracted using EtOAc (3×15 mL). The combined organic layer was dried over anhydrous Na$_2$SO$_4$ and the solvent was evaporated under vacuo and the residue was purified by column chromatography on silica gel using EtOAc in Hexanes (30-50% EA in Hx) as solvent gradient to give pure Compound 7 (93 mg, 12%, 25% based on trans olefin ester as a light yellow solid. TLC (EtOAc:Hexane=4:6) Rf0.35, HPLC purity 98%, $^1$H NMR (500 MHz, CDCl$_3$): δ 7.12 (d, J=7.5 Hz, 1H), 7.03 (s, 1H), 6.93 (d, J=7.5 Hz, 1H), 5.35 (s, 1H), 3.67 (s, 3H), 2.88-2.52 (m, 4H), 2.49-2.45 (m, 2H), 2.44-2.17 (m, 2H), 2.12-2.10 (m, 1H), 2.09-2.02 (m, 4H), 1.72-1.67 (m, 2H); $^{13}$C NMR (125 MHz, CDCl$_3$) δ 199.3, 178.0, 144.5, 141.8, 139.3, 126.0, 124.2, 102.0, 55.6, 43.1, 37.5, 35.2, 33.0, 32.7, 32.5, 32.4, 25.5; ESI-MS (positive): m/z 271.1.

Example 4

Synthesis of Compound 11

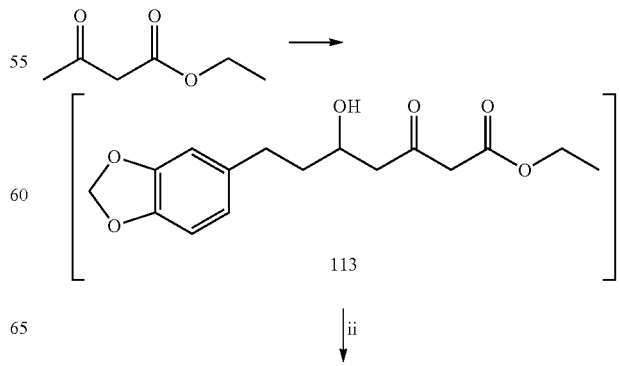

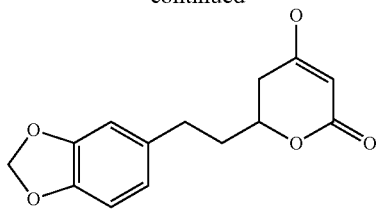

Compound 11

Reagents and conditions:(i) (a) NaH, BuLi, dry THF, 0° C., 30 min, (b) compound 108, −55° C. to RT, 6 h; (ii) (a) K₂CO₃, MeOH, RT, 6 h, (b) Dil. HCl, 64%.

Ethylacetoacetate (2.97 mmol) was added drop-wise to a slurry of sodium hydride (5.66 mmol) in dry THF (15 mL) under nitrogen atmosphere at 0° C. and stirred at same temperature for 30 min. Then n-BuLi (5.66 mmol) was added drop wise over a period of 10 min and further stirred for another 30 min at 0° C. The reaction mixture was brought to −55° C., and compound 108 in dry THF (8 mL) was added dropwise. After 30 min reaction temperature was brought to room temperature and stirred for 6 hours. Upon completion, reaction mixture was quenched by the addition of saturated NH₄Cl (10 mL) and was extracted with ethyl acetate (2×10 mL). Organic layers were combined, dried over anhydrous MgSO₄. The solvent was evaporated in vacuo to give aldol adduct δ-hydroxy-β-ketoester 113. Anhydrous K₂CO₃ (5.94 mml) was added to aldol adduct δ-hydroxy-β-ketoester 113 in methanol (15 mL) at room temperature and stirred for 6 h. Upon reaction completion, methanol was removed under reduced pressure followed by dil HCl (10 mL) and ethyl acetate (10 mL) was added. Layer separation was done, extracted the compound with EtOAc (2×10 mL). The combined organic layer was dried over anhydrous MgSO₄ and was evaporated in vacuo and the residue was purified by column chromatography on silica gel using EtOAc in Hexanes (30-50% EA in Hexanes) as solvent gradient to give pure compound Compound (495 mg, 64%) as a light yellow solid. TLC (EtOAc:Hexane=7:3) Rf 0.34, (2:1 mixture of Keto-Enol tautomers), HPLC purity 95%. ¹H NMR (500 MHz, CDCl₃): δ 6.72 (d, J=8.0 Hz, 1H), 6.65 (d, J=8.0 Hz, 0.5H), 6.67 (d, J=8.0 Hz, 1H), 6.61 (d, J=8.0 Hz, 0.5H), 5.93 (s, 2H), 5.91 (s, 0.5H), 3.50 (AB quartet, J=18.0 Hz, 2H), 2.84-2.77 (m, 1H), 2.74-2.69 (m, 1H), 2.65 (dd, J=18.5, 3.0 Hz, 1H), 2.55-2.42 (m, 2H), 2.10-2.01 (m, 2H), 1.97-1.92 (m, 1H); ¹³C NMR (125 MHz, CDCl₃) δ 199.8, 167.2, 148.0, 146.2, 133.8, 121.4, 108.9, 108.5, 101.0, 100.8, 74.2, 47.2, 43.6, 36.5, 30.6; ESI-MS (positive): m/z 263.1.

Example 5

Synthesis of Compound 12

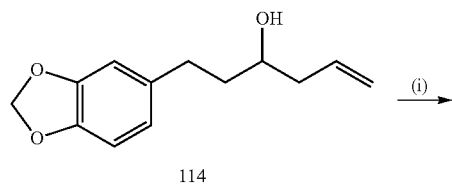

114

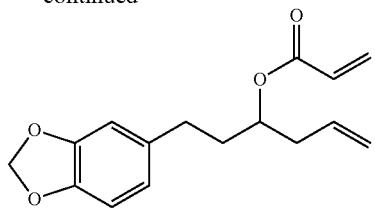

115

↓(ii)

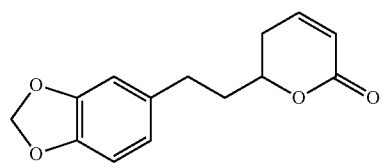

Compound 12

Reagents and conditions:(i) Et₃N, dry CH₂Cl₂; 94% (iii) Grubb's catalyst 2ⁿᵈ generation, dry CH₂Cl₂, reflux, 62%.

General procedure for acylation: To a solution of homoallylic alcohol 114 (3.21 mmol), in CH₂Cl₂ (15 mL) was cooled to 0° C. and added acryloyl chloride (3.85 mmol) followed by Et₃N (6.42 mmol). The mixture was warmed to room temperature and stirred for 2 h. The resulting mixture was filtered through a short pad of Celite, poured into water, and then the product was extracted with CH₂Cl₂ (2×10 mL). Solvent evaporation under reduced pressure and purification of this residue by column chromatography on silica gel using EtOAc in Hexanes (30-50% EA in Hexanes) as solvent gradient furnished the corresponding acrylic ester 15 (785 mg, 95%). (Ref: *Bioorganic & Medicinal Chemistry* 2006, 14, 622-631). TLC (EtOAc:Hexane=2:8) Rf=0.4. ¹H NMR (500 MHz, CDCl₃): δ 6.71 (d, J=8.0 Hz, 1H), 6.65 (d, J=1.0 Hz, 1H), 6.60 (d, J=8.0 Hz, 1H), 6.41 (dd, J=17.5, 1.5 Hz, 1H), 6.12 (dd, J=17.5, 10.5 Hz, 1H), 5.91 (s, 2H), 5.82 (dd, J=10.5, 1.5 Hz, 1H), 5.78-5.72 (m, 1H), 5.09-5.01 (m, 2H), 2.63-2.49 (m, 2H), 2.37 (t, J=6.5 Hz, 2H), 1.92-1.85 (m, 2H); ¹³C NMR (125 MHz, CDCl₃) δ 165.8, 147.6, 145.7, 135.3, 133.3, 130.5, 128.7, 121.0, 117.9, 108.7, 108.2, 100.7, 72.9, 38.6, 35.5, 31.4; ESI-MS (positive): m/z 261.1

To a stirred solution of acrylic ester 115 (1.82 mmol) in dichloromethane (10 mL) was added the Grubb's catalyst 2ⁿᵈ generation (10 mol %). The resulting mixture was heated at 55-60° C. for 18 h. After completion of reaction, the solvent was evaporated under reduced pressure. The residue was purified by column chromatography on silica gel to give the pure product compound 12 (293 mg, 62%). TLC (EtOAc:Hexane=3:7) Rf0.3, HPLC purity 98%. ¹H NMR (500 MHz, CDCl₃): δ 6.86-6.84 (m, 1H), 6.69 (d, J=7.5 Hz, 1H), 6.66 (d, J=1.0 Hz, 1H), 6.60 (d, J=8.0, 1H), 5.98 (dd, J=9.5, 1.5 Hz, 1H), 5.86 (s, 2H), 4.39-4.34 (m, 1H), 2.79-2.65 (m, 1H), 2.63-2.31 (m, 1H), 2.30-2.08 (m, 2H), 2.07-2.01 (m, 1H), 1.89-1.87 (m, 1H); ¹³C NMR (125 MHz, CDCl₃) δ 164.4, 147.6, 145.8, 145.1, 134.6, 121.3, 121.2, 108.8, 108.2, 100.8, 76.77, 36.6, 30.6, 29.4; ESI-MS (positive): m/z 247.0.

Example 6

Synthesis of Compound 15

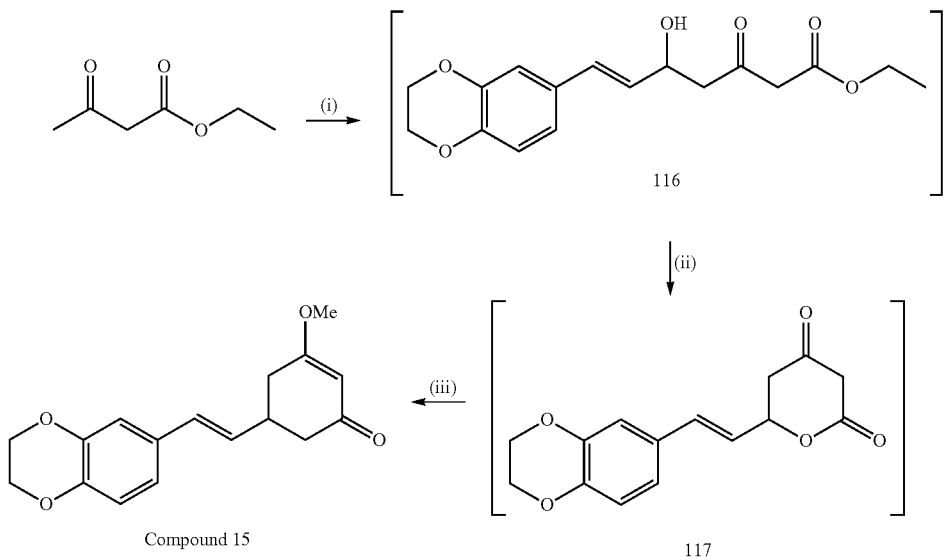

Reagents and conditions:(i) (a) NaH, BuLi, dry THF, 0° C., 30 min, (b) (E)-3-(2,3-dihydrobenzo[b][1,4]dioxin-6-yl)acrylaldehyde, −55° C. to RT, 6 h; (ii) (a) $K_2CO_3$, MeOH, RT, 6 h, (iii) Dimethyl sulfate, acetone, RT, 12 h, 65%.

Ethylacetoacetate (4.21 mmol) was added drop wise to a slurry of sodium hydride (8.42 mmol) in dry THF (15 mL) under nitrogen atmosphere at 0° C. and stirred at same temperature for 30 min. Followed by n-BuLi (8.42 mmol) was added drop wise over a period of 10 min and further stirred for another 30 min at 0° C. The reaction mixture was brought to −55° C., and (E)-3-(2,3-dihydrobenzo[b][1,4]dioxin-6-yl)acrylaldehyde[4] (4.21 mmol) in dry THF (8 mL) was added dropwise. After 30 min reaction temperature was brought to room temperature and stirred for 6 h. Upon completion, reaction mixture was quenched by the addition of saturated $NH_4Cl$ (10 mL) and was extracted with ethyl acetate (2×10 mL). Organic layers were combined, dried over anhydrous $MgSO_4$. The solvent was evaporated in vacuo to give aldol adduct δ-hydroxy-β-ketoester 116. Anhydrous $K_2CO_3$ (8.42 mml) was added to aldol adduct δ-hydroxy-β-ketoester 116 in methanol (15 mL) at room temperature and stirred for 6 hours. Upon reaction completion, methanol was removed under reduced pressure. The residue was redissolved in anhydrous acetone (15 mL) and subsequently dimethylsulfate (8.42 mmol) was added, stirred at room temperature for 12 hours. The solvent was removed under reduced pressure and diluted with EtOAc (10 mL) and water (10 mL) followed by EtOAc extraction (2×10 mL). The combined organic layers were dried over anhydrous $MgSO_4$. Solvent was evaporated in vacuo and the residue was purified by column chromatography on silica gel using EtOAc in Hexanes (30-50% EA in Hx) as solvent gradient to give pure Compound 116 (788 mg, 65%) as a light yellow solid. TLC (EtOAc:Hexane=3:7) Rf0.4, HPLC purity 95%. $^1$H NMR (500 MHz, $CDCl_3$): δ 6.88 (d, J=1.5 Hz, 1H), 6.87 (d, J=1.5 Hz, 1H), 6.81 (d, J=8.0 Hz, 1H), 6.59 (d, J=15.5 Hz, 1H), 6.10 (dd, J=16.0, 6.5 Hz, 1H), 5.18 (s, 1H), 5.03-4.99 (m, 1H), 4.25 (s, 4H), 3.76 (s, 3H), 2.67-2.61 (m, 1H), 2.54 (dd, J=17.0, 4.0 Hz, 1H); $^{13}$C NMR (125 MHz, $CDCl_3$) δ 172.3, 166.8, 143.9, 143.5, 132.7, 129.4, 123.8, 120.2, 117.4, 115.3, 90.5, 76.0, 64.4, 64.3, 56.0, 33.3, 29.3; ESI-MS (positive): m/z 289.0.

Example 7

Synthesis of Compound 14

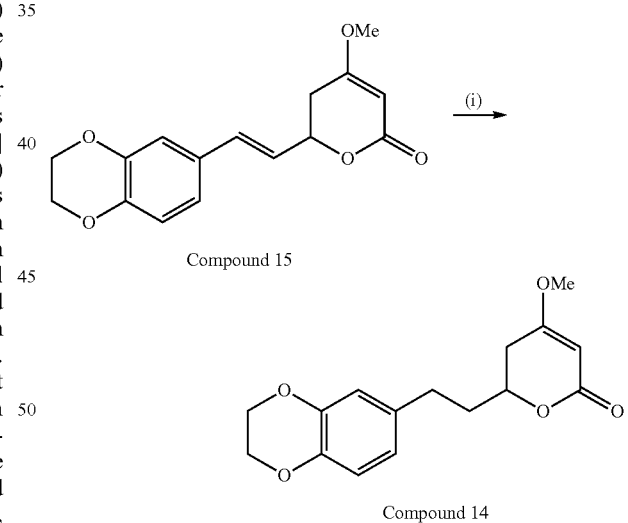

Reagents and conditions:(i) $H_2$, Pd/C (1 atm), THF, 2 h, 94%

To a stirred solution of compound 15 (0.86 mmol) in THF (5 mL) was added Pd/C (5% wt) under $N_2$ atmosphere. The flask was degassed under vacuum and the reaction was carried out under $H_2$ atmosphere at 1 atm pressure ($H_2$ balloon) for 2 h. After completion, the reaction was filtered through the celite bed, washed the celite bed using EtOAC (2×5 mL) and combined organic layers were dried over anhydrous $MgSO_4$. The solvent was evaporated in vacuo and the residue was purified by column chromatography on silica gel using EtOAc in Hexanes (20-50% EA in Hx) as solvent gradient to give pure compound 14 (237 mg, 94%) as a light yellow solid. TLC (EtOAc:Hexane=4:6) Rf0.35, HPLC purity 98%. $^1$H NMR (500 MHz, CDCl$_3$): δ 6.70 (d, J=2.0 Hz, 1H), 6.67 (d, J=1.5 Hz, 1H), 6.65 (d, J=2.0 Hz, 1H), 5.13 (d, J=1.0 Hz, 1H), 4.38-4.32 (m, 1H), 4.23 (s, 4H), 3.72 (s, 3H), 2.79-2.66 (m, 1H), 2.65-2.49 (m, 1H), 2.48-2.46 (m, 1H), 2.27 (dd, J=17.0, 4.0 Hz, 1H), 2.11-2.04 (m, 1H), 1.91-1.90 (m, 1H); $^{13}$C NMR (125 MHz, CDCl$_3$) δ 172.7, 167.2, 143.4, 141.8, 134.0, 121.3, 117.1, 117.0, 90.3, 74.7, 64.4, 64.3, 55.9, 36.3, 33.0, 30.2; ESI-MS (positive): m/z 291.0.

Preparation of Compound 118

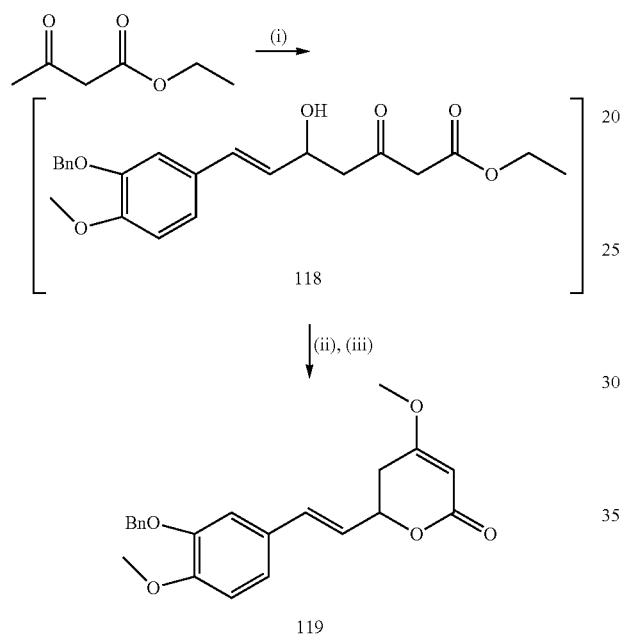

Reagents and conditions:(i) (a) NaH, BuLi, dry THF, 0° C., 30 min, (b) (E)-3-(3-(benzyloxy)-4-methoxyphenyl)acrylaldehyde, −55° C. to RT, 6 h; (ii) (a) K$_2$CO$_3$, MeOH, RT, 6 h, (b) Dimethyl sulfate, acetone, RT, 12 h, 65%.

To a stirred suspension of sodium hydride (3.73 mmol) in dry THF (10 mL) was added ethylacetoacetate (1.86 mmol) under nitrogen atmosphere at 0° C. and stirred at same temperature for 30 min. Followed by n-BuLi (3.73 mmol) was added drop wise over a period of 10 min and further stirred for another 30 min at 0° C. The reaction mixture was cooled to −55° C., and (E)-3-(3-(benzyloxy)-4-methoxyphenyl)acrylaldehyde (1.86 mmol) in dry THF (5 mL) was added dropwise. After 30 min reaction temperature was brought to room temperature and stirred for 6 h. Upon completion, was quenched by the addition of saturated NH$_4$Cl (10 mL) and was extracted with ethyl acetate (2×10 mL). Organic layers were combined, dried over anhydrous MgSO$_4$. The solvent was evaporated in vacuo to give aldol adduct δ-hydroxy-β-ketoester 118. Anhydrous K$_2$CO$_3$ (3.73 mml) was added to aldol adduct δ-hydroxy-β-ketoester 118 in methanol (10 mL) at room temperature and stirred for 6 hours. Upon reaction completion, methanol was removed under reduced pressure followed by the reaction mass was dissolved in anhydrous acetone (10 mL) and subsequently was added dimethylsulfate (3.73 mmol), the reaction mixture was stirred at room temperature for 12 h. The solvent was removed under reduced pressure and diluted with EtOAc (10 mL) and water (10 mL) followed by EtOAc extraction (2×10 mL). The combined organic layers were dried over anhydrous MgSO$_4$. Solvent was evaporated in vacuo and the residue was purified by column chromatography on silica gel using EtOAc in Hexanes (20-50% EA in Hx) as solvent gradient to give pure compound 119 (443 mg, 65%) as a light yellow solid. TLC (EtOAc:Hexane=4:6) Rf0.4, HPLC purity 98%. $^1$H NMR (500 MHz, CDCl$_3$): δ 7.47 (d, J=7.0 Hz, 2H), 7.40-7.37 (m, 2H), 7.34-7.28 (m, 1H), 6.99 (d, J=1.5 Hz, 1H), 6.97 (d, J=8.5 Hz, 1H), 6.87 (d, J=8.0 Hz, 1H), 6.62 (d, J=16.0 Hz, 1H), 6.06 (dd, J=16.0, 6.5 Hz, 1H), 5.20 (s, 1H), 5.17 (s, 2H), 5.05-5.00 (m, 1H), 3.90 (s, 3H), 3.77 (s, 3H), 2.65 (dd, J=17.0, 4.5 Hz, 1H), 2.53 (dd, J=17.0, 4.5 Hz, 1H); $^{13}$C NMR (125 MHz, CDCl$_3$) δ 172.4, 166.9, 150.1, 148.2, 136.9, 132.9, 128.7, 128.6, 127.9, 127.3, 123.4, 120.6, 112.0, 111.7, 90.5, 76.0, 71.1, 56.1, 56.0, 33.3, 29.3; ESI-MS (positive): m/z 367.1.

Example 8

Synthesis of Compound 6

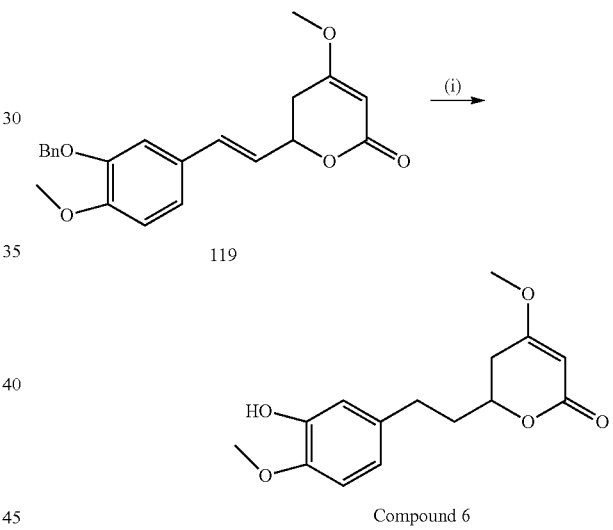

Reagents and conditions:(i) H$_2$, Pd/C (1 atm), THF, 2 h, 95%.

To a stirred solution of compound 119 (1.0 mmol) in THF (5 mL) was added, Pd/C (5% wt) under N$_2$ atmosphere. The flask was degassed under vacuum and the reaction was carried out under H$_2$ atmosphere at 1 atm pressure (H$_2$ balloon) for 2 h. After completion, the reaction was filtered through the celite bed, washed the celite bed using EtOAC (2×5 mL) and combined organic layers were dried over anhydrous MgSO$_4$. The solvent was evaporated in vacuo and the residue was purified by column chromatography on silica gel using EtOAc in Hexanes (30-50% EA in Hx) as solvent gradient to give pure compound 6 (264 mg, 95%) as a white solid. TLC (EtOAc:Hexane=4:6) Rf0.3, HPLC purity 97%. $^1$H NMR (500 MHz, CDCl$_3$): δ 6.77-6.66 (m, 2H), 6.63 (d, J=8.0 Hz, 1H), 5.61 (s, 1H), 5.13 (s, 1H), 4.37-4.32 (m, 1H), 3.86 (s, 3H), 3.72 (s, 3H), 2.77-2.74 (m, 1H), 2.72-2.67 (m, 1H), 2.48 (dd, J=17.0, 12.5 Hz, 1H), 2.29 (dd, J=17.0, 4.0 Hz, 1H), 2.11-2.04 (m, 1H), 1.91-1.85 (m, 1H); $^{13}$C NMR (125 MHz, CDCl$_3$) δ 172.7, 167.3, 145.6, 144.9, 134.0, 119.9, 114.5, 110.7, 90.3, 74.7, 56.0, 36.3, 33.0, 30.3; ESI-MS (positive): m/z 279.1.

Examples 9, 10, and 11

Synthesis of Compounds 8, 10, and 13

General Reaction Procedure for the Synthesis of Compound 8, 10, 13:

In first step, ethylacetoacetate (1 mmol) was added dropwise to a slurry of sodium hydride (2 mmol) in dry THF (5 mL) under nitrogen atmosphere at 0° C. and stirred at same temperature for 30 min. Followed by n-BuLi (2 mmol) was added drop wise over a period of 10 min and further stirred for another 30 min at 0° C. The reaction mixture was cooled to −55° C., followed by cinnamaldehyde/ketone 219 (1 mmol,) in dry THF (5 mL) was added drop wise. After 30 min reaction mixture was brought up to room temperature and stirred further for 6 h. Reaction mixture was quenched with saturated aqueous ammonium chloride solution (5 mL) upon completion as judged by TLC and extracted with ethyl acetate (2×10 mL). Organic layers were combined, washed with saturated brine solution and dried over anhydrous $MgSO_4$. The solvent was evaporated in vacuo to give aldol adduct δ-hydroxy-β-ketoester 121.

In second step, anhydrous $K_2CO_3$ (2 mmol) was added to aldol adduct δ-hydroxy-β-ketoester 121 in methanol (5 mL) at room temperature and stirred for 2 hours. Upon reaction completion, methanol was removed under reduced pressure and the reaction mass was redissolved in anhydrous acetone (5 mL) followed dimethyl sulfate (2 mmol) was added. The reaction mixture was stirred at room temperature for 12 h and diluted with ethyl acetate (5 mL); organic layer was washed with 1N HCl and dried over anhydrous $MgSO_4$. The solvent was evaporated in vacuo to afford unsaturated lactone 123 and were subjected to hydrogenation without further purification. The compound 123 (1.0 mmol) in THF (5 mL) was added Pd/C (5% wt) under $N_2$ atmosphere. The flask was degassed under vacuum and the reaction was carried out under $H_2$ atmosphere at 1 atm pressure ($H_2$ balloon) for 2 h. After completion, the reaction was filtered through the celite bed, washed the celite bed using EtOAC (2×5 mL) and combined organic layers were dried over anhydrous $MgSO_4$ and purified by column chromatography on silica gel using EtOAc in Hexanes (30-50% EA in Hx) as solvent gradient to give pure compounds 8, 10, and 13 (62-64% yield) as a light yellow solid.

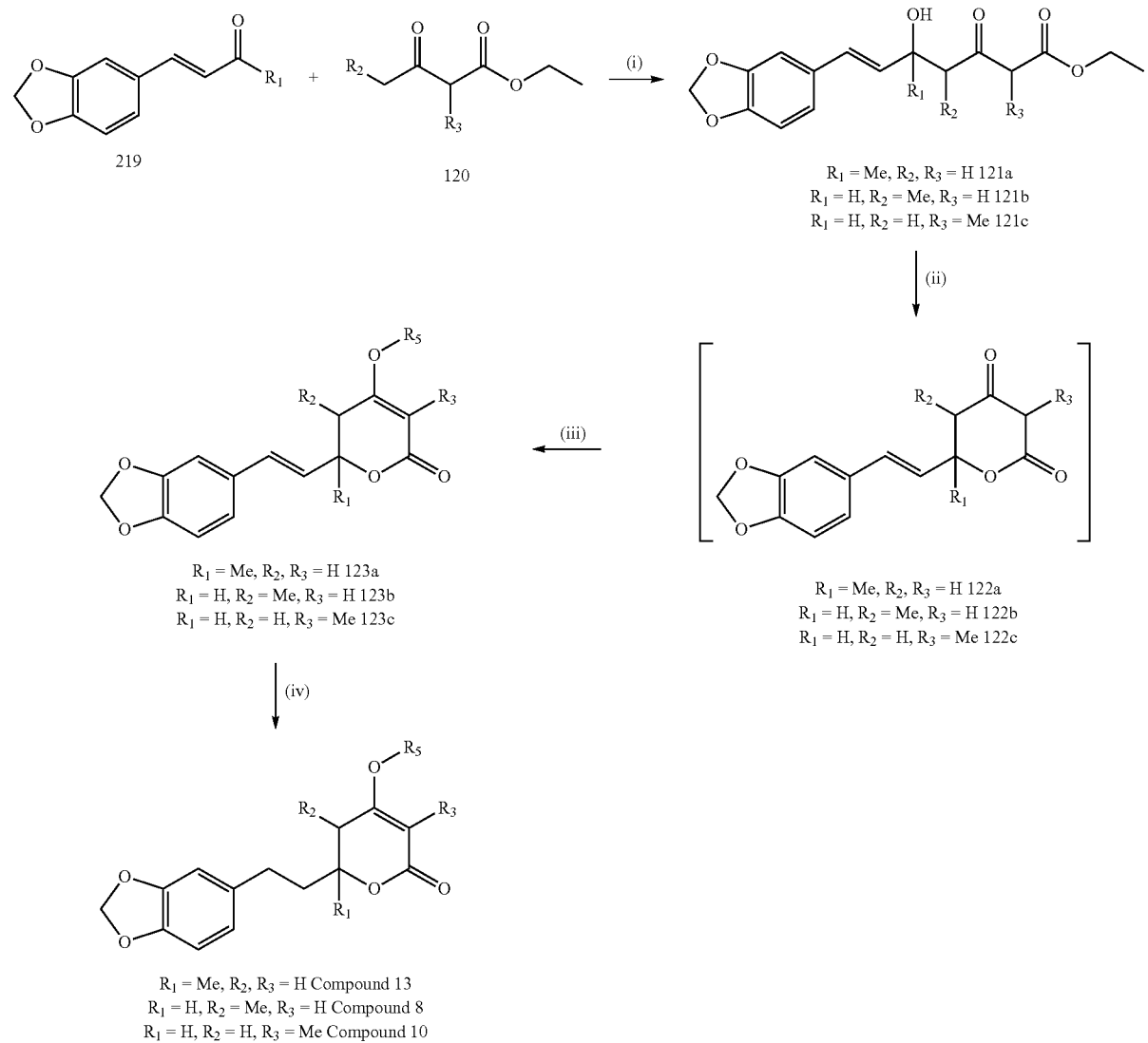

$R_1$ = Me, $R_2$, $R_3$ = H 121a
$R_1$ = H, $R_2$ = Me, $R_3$ = H 121b
$R_1$ = H, $R_2$ = H, $R_3$ = Me 121c $R_1$ = Me, $R_2$, $R_3$ = H 122a
$R_1$ = H, $R_2$ = Me, $R_3$ = H 122b
$R_1$ = H, $R_2$ = H, $R_3$ = Me 122c $R_1$ = Me, $R_2$, $R_3$ = H 123a
$R_1$ = H, $R_2$ = Me, $R_3$ = H 123b
$R_1$ = H, $R_2$ = H, $R_3$ = Me 123c $R_1$ = Me, $R_2$, $R_3$ = H Compound 13
$R_1$ = H, $R_2$ = Me, $R_3$ = H Compound 8
$R_1$ = H, $R_2$ = H, $R_3$ = Me Compound 10

Compound 8: Obtained as light yellow solid (185 mg, 64%), TLC (EtOAc:Hexane=4:6) Rf 0.35, HPLC purity 99.2%. $^1$H NMR (500 MHz, CDCl$_3$): δ 6.64 (d, J=8.0 Hz, 1H), 6.61 (s, 1H), 6.57, (d, J=8.0 Hz, 1H), 5.04 (s, 1H), 5.00 (s, 1H), 4.25-4.22 (m, 1H), 4.00-3.96 (m, 1H), 3.65 (s, 3H), 3.64 (s, 3H), 2.75-2.69 (m, 2H), 2.61-2.54 (m, 2H), 2.40 (quint, J=7.0 Hz, 1H), 2.22-2.19 (m, 1H), 2.02-1.96 (m, 1H), 1.93-1.91 (m, 1H), 1.85-1.83 (m, 1H), 1.09 (d, J=7.0 Hz, 3H), 1.05 (d, J=7.0 Hz, 3H); $^{13}$C NMR (125 MHz, CDCl$_3$) δ 178.4, 175.5, 167.0, 166.2, 147.5, 147.4, 145.6, 145.5, 134.6, 134.4, 121.0, 108.64, 108.60, 108.0, 107.9, 100.6, 100.5, 89.1, 88.8, 80.0, 76.9, 55.96, 55.92, 36.2, 36.0, 34.7, 32.7, 30.8, 30.6, 13.7, 10.6; ESI-MS (positive): m/z 291.1.

Compound 10: Obtained as light yellow solid (185 mg, 64%), TLC (EtOAc:Hexane=4:6) Rf 0.35, HPLC purity 99.1%. $^1$H NMR (500 MHz, CDCl$_3$): δ 6.73 (dd, J=8.0, 4.0 Hz, 1H), 6.69 (s, 1H), (d, J=8.0 Hz, 1H), 5.91 (d, J=4.0 Hz, 1H), 4.29-4.24 (m, 1H), 2.83-2.78 (m, 1H), 2.74-2.69 (m, 1H), 2.53-2.46 (m, 2H), 2.11-2.06 (m, 1H), 1.89-1.86 (m, 1H), 1.77 (d, J=1.0 Hz, 1H); $^{13}$C NMR (125 MHz, CDCl$_3$) δ 168.5, 165.2, 147.7, 145.8, 134.6, 121.3, 108.8, 108.3, 100.8, 73.3, 55.4, 36.8, 30.7, 29.3, 8.9; ESI-MS (positive): m/z 291.1.

Compound 13: Obtained as light yellow solid (180 mg, 62%), TLC (EtOAc:Hexane=4:6) Rf 0.35, HPLC purity 98.8%. $^1$H NMR (500 MHz, CDCl$_3$): δ 6.65 (d, J=8.0 Hz, 1H), 6.60 (d, 1.0 Hz, 1H), 6.56 (d, J=8.0 Hz, 1H), 5.83 (s, 2H), 5.11 (s, 1H), 3.68 (s, 3H), 2.63-2.57 (m, 2H), 2.53 (d, J=17.5 Hz, 1H), 2.30 (d, J=17.5 Hz, 1H), 1.98-1.92 (m, 1H), 1.88-1.83 (m, 1H), 1.40 (s, 3H); $^{13}$C NMR (125 MHz, CDCl$_3$) δ 171.3, 166.3, 147.4, 145.5, 134.9, 120.8, 108.5, 108.0, 100.6, 89.5, 79.4, 55.8, 42.4, 37.2, 29.4, 24.7; ESI-MS (positive): m/z 291.1.

Example 12

Synthesis of Compound 68

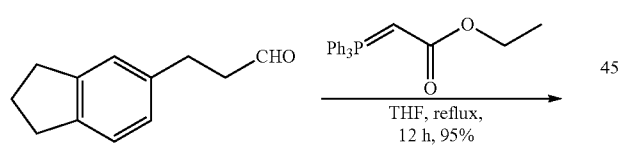

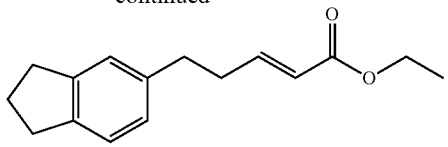

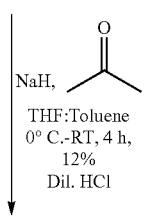

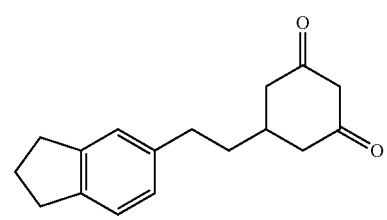

68

By following the similar synthetic sequence to the sequence used to prepare compound 7, compound 68 was prepared. TLC (EtOAc:Hexane=4:6) Rf0.35. $^1$H NMR (500 MHz, CDCl$_3$): δ 7.19 (d, J=8.0 Hz, 1H) 7.11 (s, 1H), 7.01 (d, J=8.0 Hz, 1H), 5.45 (s, 1H), 3.72 (s, 3H), 3.34-3.29 (m, 1H), 2.91-2.67 (m, 4H), 2.66-2.52 (m, 4H), 2.10-2.07 (m, 2H); $^{13}$C NMR (125 MHz, CDCl$_3$) δ 198.9, 177.8, 144.9, 143.1, 140.6, 124.6, 124.5, 122.6, 102.1, 55.8, 44.2, 39.3, 36.7, 32.8, 32.4, 25.4; ESI-MS (positive): m/z 243.1.

Example 13

Synthesis of Compound 82

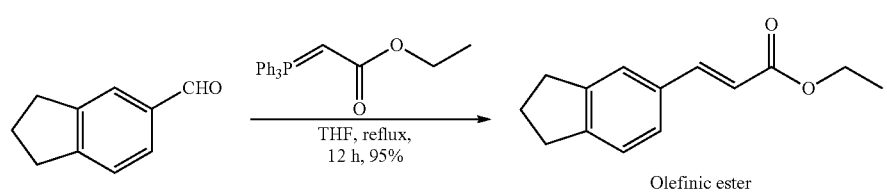

Olefinic ester

-continued

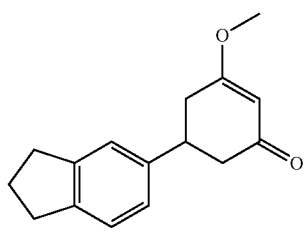 [SMILES: COC1=CC(=O)CC(c2ccc3c(c2)CCC3)C1] 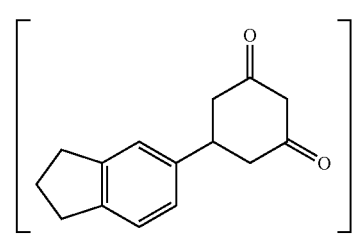

Compound 82

Using a similar synthetic sequence to the sequence used to prepare compound 7, compound 82 was prepared.

Preparation of Olefinic Ester: TLC (EtOAc:Hexane=2:8) Rf=0.4. $^1$H NMR (500 MHz, CDCl$_3$): δ 7.67 (d, J=16.0 Hz, 1H), 7.39 (s, 1H), 7.29 (d, J=8.0 Hz, 1H), 7.20 (d, J=8.0 Hz, 1H), 6.39 (d, J=16.0 Hz, 1H), 4.25 (q, J=7.5 Hz, 2H), 2.91 (t, J=7.5 Hz, 4H), 2.08 (quint, J=7.5 Hz, 2H), 1.33 (t, J=7.5 Hz, 3H); $^{13}$C NMR (125 MHz, CDCl$_3$) δ 167.3, 147.2, 145.1, 145.0, 132.6, 126.6, 124.7, 123.7, 116.8, 60.3, 32.8, 32.6, 25.4, 14.3; ESI-MS (positive): m/z 217.1.

Synthesis of Compound 82: TLC (EtOAc:Hexane=4:6) Rf=0.35, HPLC purity 98%. $^1$H NMR (500 MHz, CDCl$_3$): δ 8.54 (bs, 1H), 7.14-7.11 (m, 1H), 7.02 (s, 1H), 6.91 (d, J=7.5 Hz, 1H), 5.48 (s, 1H), 3.37 (s, 1H), 2.87-2.85 (m, 4H), 2.76 (dd, J=15.5, 4.0 Hz, 1H), 2.62 (m, 2H), 2.50 (d, J=13.0 Hz, 1H), 2.40 (dd, J=15.5, 10.5 Hz, 1H), 2.14 (d, J=11.0 Hz, 2H), 2.08-2.01 (m, 3H), 1.70-1.66 (m, 2H); $^{13}$C NMR (125 MHz, CDCl$_3$) δ 203.5, 191.8, 144.7, 144.5, 142.1, 141.8, 139.3, 138.5, 126.0, 124.3, 124.3, 124.2, 104.1, 57.9, 46.2, 38.6, 37.5, 37.1, 33.1, 32.7, 32.5, 32.4, 29.8, 25.5; ESI-MS (positive): m/z 257.1.

Examples 14-37

Synthesis of Representative Compounds of the Invention

Representative compounds of the invention (Examples 14-37) were prepared using the following general procedures.

General reaction procedure for the synthesis of substituted cinnamaldehydes: To a solution of aromatic aldehyde (1.0 equiv) in dry toluene, (triphenylphosphoranylidene)acetaldehyde (1.0 equiv) was added and the reaction mixture was stirred at 95° C. for 12 hours under N$_2$ atmosphere. Toluene was evaporated in vacuo and the residue was subjected for flash column chromatography on silica gel to give desired cinnamaldehydes. These cinnamaldehydes are known compounds with no characterization reported herein.

Method A—General reaction procedure: Synthesis of 6-substituted-4-methoxy-5,6-dihydro-2H-pyran-2-one were carried out by Hetro Diels-Alder reaction of Brassard's diene 1 with carbonyl dieneophiles using the procedure similar to that reported by Lin et al., Org. Lett., 10(6):1311-4 (2008). In brief, to a stirred solution of 4-picolyl chloride hydrochloride (0.0852 mmoles, 0.15 equiv) in dry toluene (1 mL), Ti(i-PrO)$_4$ (0.0852 mmoles, 0.15 equiv, 1 M in dry toluene) was added under N$_2$ atmosphere. Aldehyde (0.568 mmoles, 1 equiv) and Brassard's diene 1 (0.852 mmoles, 1.5 equiv) were added to the reaction mixture and further stirred for 84 hours. Trifluoroacetic acid was added to the reaction mixture, stirred for 15 min. and neutralized with saturated NaHCO$_3$. The reaction mixture was then extracted with CH$_2$Cl$_2$ (2×15 mL), organic layers were combined and washed with saturated NaCl solution and dried over anhydrous MgSO$_4$. The solvent was evaporated in vacuo and the residue was purified by flash column chromatography on silica gel to give 6-substituted-4-methoxy-5,6-dihydro-2H-pyran-2-one. Yields of these 6-substituted-4-methoxy-5,6-dihydro-2H-pyran-2-one were calculated based on un reacted aldehyde recovery (15-35%).

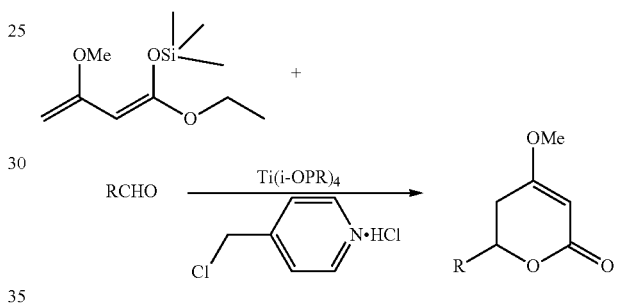

Synthesis of 6-substituted-4-methoxy-5,6-dihydro-2H-pyran-2-one Employing Method A Brassard's diene was prepared from ethyl 3-methoxybut-2-enoate according to literature reported procedure. (Smissman, E. E.; Voldeng, A. N. J Org. Chem. 1964, 29, 3161-3165.; and Savard, J.; Brassard, P. Tetrahedron Lett. 1979, 20, 4911-4914.)

Method B—General reaction procedure: Synthesis of 3,5,6-substituted-4-alkoxy-2H-pyran-2-one was achieved in two step procedure. Aldol condensation of ethylacetoacetate dianion with corresponding cinnamaldehyde/ketone yielding aldol adduct δ-hydroxy-β-ketoester and subsequent lactonization followed by O-alkylation affords 6-substituted-4-alkoxy-5,6-dihydro-2H-pyran-2-one. In first step, ethylacetoacetate (1 eq) was added drop-wise to a slurry of sodium hydride (2 eq) in dry THF under nitrogen atmosphere at 0° C. and stirred at same temperature for 30 min. Then n-BuLi (2 eq) was added drop wise over a period of 10 min and further stirred for another 30 min at 0° C. The reaction mixture was brought up to −55° C., when cinnamaldehyde/ketone (1 eq dissolved in dry THF) was added drop wise. After 30 min reaction mixture was brought up to room temperature and stirred further for 2-3 hours. Reaction mixture was quenched with saturated aqueous ammonium chloride solution upon completion as judged by TLC and extracted with ethyl acetate (2×50 mL). Organic layers were combined, washed with saturated NaCl solution and dried over anhydrous MgSO$_4$. The solvent was evaporated in vacuo and the residue was purified by flash column chromatography on silica gel to give aldol adduct δ-hydroxy-β-ketoester. In second step, anhydrous $K_2CO_3$ (2 eq) was added to aldol adduct δ-hydroxy-β-ketoester (1 eq) in methanol at room temperature and stirred for 2 hours. Upon reaction completion, methanol was removed under reduced pressure and the reaction mass was redissolved in anhydrous acetone followed by addition of alkylation agent (2 eq). The reaction mixture was stirred at room temperature for overnight and diluted with ethyl acetate; organic layer was washed with 1N HCl and dried over anhydrous $MgSO_4$. Ethyl acetate was evaporated in vacuo and the residue was purified by flash column chromatography on silica gel to give 3,5,6-substituted-4-alkoxy-2H-pyran-2-one.

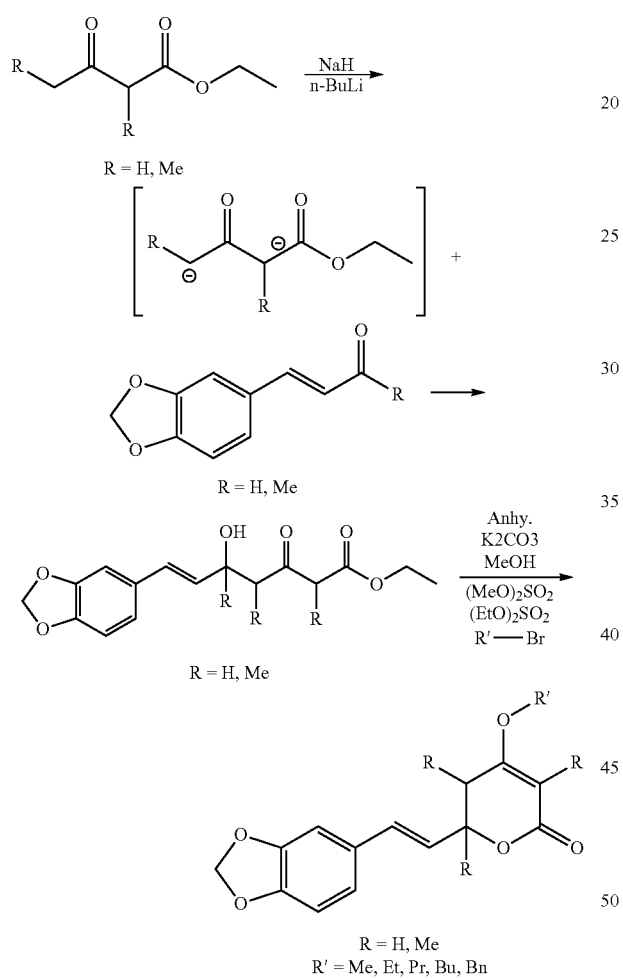

Synthesis of
3,5,6-substituted-4-alkoxy-2H-pyran-2-one
Employing Method B

Method C: Synthesis of Homoallylic Alcohols: An oven-dried flask was charged with a solution of piperonal cinnamaldehyde (1.0 mmol) in THF (10 mL), and was cooled to −78° C. under nitrogen. A solution of allylmagnesium chloride in THF (1.2 mmol.) was added dropwise, and the resulting suspension was gradually warm to rt and stirred overnight at rt. The reaction was cooled to −78° C., and saturated aqueous ammonium chloride was added to the mixture. The organic layer was separated, and the aqueous layer was extracted with ethyl acetate. The combined organic layers were dried over anhydrous $MgSO_4$, filtered and concentrated under reduced pressure. The residue was purified by silica gel flash chromatography gives homoallylic alcohol in 80% yields. (*European Journal of Medicinal Chemistry* 2011, 46, 3190-3200.)

General Procedure for Acylation: To a solution of homoallylic alcohol (1.0 mmol), obtained as described above, in $CH_2Cl_2$ and cooled to 0° C. were added acryloyl chloride (1.2 mmol) and $Et_3N$ (1.2 mmol). The mixture was warmed to room temperature and stirred for 2-4 h. The resulting mixture was filtered through a short pad of Celite, poured into water, and then the product was extracted with $CH_2Cl_2$. Solvent evaporation under reduced pressure and purification of this residue by column chromatography on silica gel furnished the corresponding acrylic esters. (Ref: *Bioorganic & Medicinal Chemistry* 2006, 14, 622-631.)

General Procedure for Ring Closing Metathesis: To a stirred solution of Grubb's catalyst $2^{nd}$ generation (10 mol %) in dichloromethane at 55-60° C. was added the acrylic ester (1 eq), obtained as described above, dissolved in dichloromethane (65 mL). The resulting mixture was heated for 12-18 h. After this period, the mixture was cooled at room temperature and evaporated under reduced pressure. The residue was purified by column chromatography on silica gel to give the product.

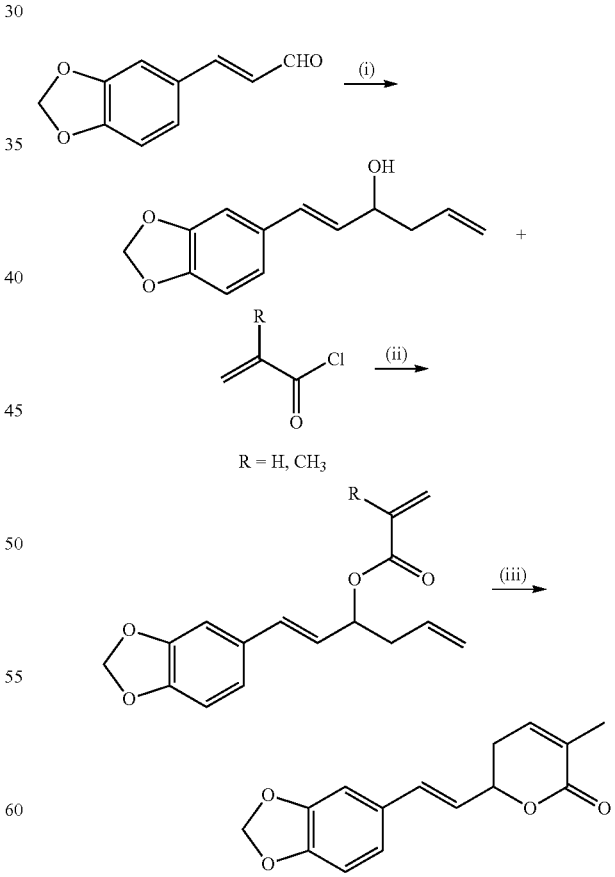

Reagents and conditions: (i) Allylmagnesium chloride, dry THF, −78° C.; (ii) Et3N, dry $CH_2Cl_2$; (iii) Grubb's catalyst $2^{nd}$ generation, dry $CH_2Cl_2$, reflux.

Example 14

6-(benzo[d][1,3]dioxol-5-yl)-4-methoxy-5,6-dihydro-2H-pyran-2-one (Compound 74)

Yield: 53%, TLC (EtOAc:Hexane=1:1) Rf=0.39, White solid, $^1$H NMR (400 MHz, CDCl$_3$): δ 6.85 (1H, d, J=1.4 Hz, Ar—), 6.79 (1H, dd, J=8.0, 1.4 Hz, Ar—), 6.73 (1H, d, J=8.0 Hz, Ar—), 5.90 (2H, s, —OCH$_2$O—), 5.25 (1H, dd, J=12.2, 4.1 Hz, —O—CH(—Ar)—CH$_2$), 5.16 (1H, d, J=1.4 Hz —C(=O)—CH=C—), 3.71 (3H, s, —OCH$_3$), 2.72 (1H, ddd, J=17.2, 12.4, 1.4 Hz, =C(—OCH$_3$)—CH$_2$—), 2.46 (1H, dd, J=17.2, 4.0 Hz, =C(—OCH$_3$)—CH$_2$—); $^{13}$C NMR (100 MHz, CDCl$_3$): 172.5, 166.8, 147.9, 147.8, 132.0, 119.8, 108.2, 106.7, 101.3, 90.5, 76.6, 56.1, 35.1; ESI-MS (positive): m/z 249 (M+1)$^+$.

Example 15

(E)-6-{2-(2,3-dihydrobenzo[b][1,4]dioxol-6-yl)vinyl}-4-methoxy-5,6-dihydro-2H-pyran-2-one (Compound 40)

Yield: 54%, TLC (EtOAc:Hexane=1:1) Rf=0.34, White solid, $^1$H NMR (400 MHz, CDCl$_3$): δ 6.84 (1H, d, J=1.8 Hz, Ar—), 6.81 (1H, dd, J=8.2, 1.8 Hz, Ar—), 6.7 (1H, d, J=8.2 Hz, Ar—), 6.53 (1H, d, J=15.8 Hz, Ar—CH=CH—), 6.03 (1H, dd, J=15.8, 6.4 Hz, Ar—CH=CH—), 5.10 (1H, d, J=1.4 Hz, —C(=O)—CH=C—), 4.91-4.99 (1H, m, —O—CH(CH=)—CH$_2$), 4.19 (4H, s, —OCH$_2$—CH$_2$O—), 3.69 (3H, s, —OCH$_3$), 2.58 (1H, ddd, J=17.2, 10.9, 1.4 Hz, =C(—OCH$_3$)—CH$_2$—), 2.45 (1H, dd, J=17.2, 4.3 Hz, =C(—OCH$_3$)—CH$_2$—); $^{13}$C NMR (100 MHz, CDCl$_3$): δ 172.3, 166.8, 143.8, 143.5, 132.7, 129.5, 123.8, 120.2, 117.4, 115.3, 90.6, 76.0, 64.4, 94.3, 56.0, 33.3; ESI-MS (positive): m/z 311 (M+23)$^+$.

Example 16

(E)-6-(4-fluorostyryl)-4-methoxy-5,6-dihydro-2H-pyran-2-one (Compound 38)

Yield: 61%, TLC (EtOAc:Hexane=1:1) Rf=0.38, Pale yellow solid, $^1$H NMR (400 MHz, CDCl$_3$): δ 7.32-7.26 (2H, m, Ar—), 6.95 (2H, t, J=8.6 Hz, Ar—), 6.64 (1H, d, J=15.8 Hz, Ar—CH=CH—), 6.10 (1H, dd, J=15.8, 6.6 Hz, Ar—CH=CH—), 5.13 (1H, d, J=1.3 Hz, —C(=O)—CH=C—), 5.0-4.93 (1H, m, —O—CH(CH=)—CH$_2$), 3.70 (3H, s, —OCH$_3$), 2.59 (1H, ddd, 17.2, 10.8, 1.3 Hz, =C(—OCH$_3$)—CH$_2$—), 2.47 (1H, dd, J=17.4, 4.6 Hz, =C(—OCH$_3$)—CH$_2$—); $^{13}$C NMR (100 MHz, CDCl$_3$): δ 172.2, 166.6, 163.9, 132.0, 131.9, 128.3, 128.2, 125.2, 115.7, 115.5, 90.6, 75.7, 56.1, 33.3; ESI-MS (positive): m/z 249 (M+1)+.

Example 17

(E)-6-(4-bromostyryl)-4-methoxy-5,6-dihydro-2H-pyran-2-one (Compound 39)

Yield: 67%, TLC (EtOAc:Hexane=1:1) Rf=0.39, Pale yellow solid, $^1$H NMR (400 MHz, CDCl$_3$): δ 7.39 (2H, d, J=8.4 Hz, A Ar—), 7.18 (2H, d, J=8.4 Hz, Ar—), 6.6 (1H, d, J=15.8 Hz, Ar—CH=CH—), 6.17 (1H, dd, J=15.9, 6.4 Hz, Ar—CH=CH—), 5.12 (1H, d, J=1.5 Hz, —C(=O)—CH=C—), 5.01-4.94 (1H, m, —O—CH(CH=)—CH$_2$), 3.70 (3H, s, —OCH$_3$), 2.58 (1H, ddd, J=17.2, 10.8, 1.3 Hz, =C(—OCH$_3$)—CH$_2$—), 2.47 (1H, dd, J=17.3, 4.4 Hz, =C(—OCH$_3$)—CH$_2$—); $^{13}$C NMR (100 MHz, CDCl$_3$): δ 172.1, 166.5, 134.6, 131.9, 131.8, 131.7, 128.2, 128.0, 126.2, 122.2, 90.5, 75.5, 56.1, 33.2; ESI-MS (positive): m/z 309 (M)$^+$, 311 (M+2)+.

Example 18

(E)-4-methoxy-6-{4-(trifluoromethyl) styryl}-5,6-dihydro-2H-pyran-2-one (Compound 41)

Yield: 72%, TLC (EtOAc:Hexane=1:1) Rf=0.40, Pale yellow solid, $^1$H NMR (400 MHz, CDCl$_3$): δ 7.52 (2H, d, J=8.0 Hz, Ar—), 7.42 (2H, d, J=8.0 Hz, Ar—), 6.72 (1H, d, J=15.7 Hz, Ar—CH=CH—), 6.29 (1H, dd, J=15.6, 6.2 Hz, Ar—CH=CH—), 5.14 (1H, d, J=1.3 Hz, —C(=O)—CH=C—), 5.04-4.97 (1H, m, —O—CH(CH=)—CH$_2$), 3.71 (3H, s, —OCH$_3$), 2.60 (1H, ddd, J=17.2, 10.8, 1.4 Hz, =C(—OCH$_3$)—CH$_2$—), 2.50 (1H, dd, J=17.2, 4.4 Hz, =C(—OCH$_3$)—CH$_2$—); $^{13}$C NMR (100 MHz, CDCl$_3$): δ 172.1, 166.6, 139.2, 131.5, 130.2, 129.9, 128.0, 126.8, 125.6, 125.3, 122.6, 90.6, 75.3, 56.1, 33.2; ESI-MS (positive): m/z 299 (M+1)$^+$.

Example 19

(E)-4-methoxy-6-(2-(napthalen-2-yl)vinyl)-5,6-dihydro-2H-pyran-2-one (Compound 42)

Yield: 72%, TLC (EtOAc:Hexane=1:1) Rf=0.42, Pale yellow solid, $^1$H NMR (400 MHz, CDCl$_3$): δ 7.81-7.78 (3H, m, Ar—), 7.76 (1H, dd, J=1.8, 8.6 Hz, Ar—), 7.48-7.45 (2H, m, Ar—), 6.88 (1H, d, J=15.9 Hz, Ar—CH=CH—), 6.38 (1H, dd, J=15.9, 6.2 Hz, Ar—CH=CH—), 5.22 (1H, d, J=1.3 Hz, —C(=O)—CH=C—), 5.14-5.09 (1H, m, —O—CH(CH=)—CH$_2$), 3.78 (3H, s, —OCH$_3$), 2.72 (1H, ddd, J=17.1, 10.8, 1.4 Hz, =C(—OCH$_3$)—CH$_2$—), 2.57 (1H, dd, J=17.2, 4.4 Hz, =C(—OCH$_3$)—CH$_2$—); $^{13}$C NMR (100 MHz, CDCl$_3$): δ 172.2, 166.7, 133.4, 133.2, 133.1, 128.4, 128.3, 128.1, 127.7, 127.2, 126.4, 126.3, 125.8, 123.3, 90.6, 75.9, 56.1, 33.3; ESI-MS (positive): m/z 303 (M+23)$^+$.

Example 20

(E)-4-methoxy-6-(2-(napthalen-1-yl)vinyl)-5,6-dihydro-2H-pyran-2-one (Compound 46)

Yield: 69%, TLC (EtOAc:Hexane=1:1) Rf=0.42, Pale yellow solid, $^1$H NMR (400 MHz, CDCl$_3$): δ 8.08 (1H, d, J=8.7 Hz, Ar—), 7.80-7.86 (2H, m, Ar—), 7.59 (1H, d, J=6.9 Hz, Ar—CH=CH—), 7.43-7.53 (4H, m, Ar—), 6.30 (1H, dd, J=15.8, 6.1 Hz, Ar—CH=CH—), 5.23 (1H, d, J=1.3 Hz, —C(=O)—CH=C—), 5.21-5.16 (1H, m, —O—CH(CH=)—CH$_2$), 3.78 (3H, s, —OCH$_3$), 2.73 (1H, ddd, J=17.1, 10.8, 1.3 Hz, =C(—OCH$_3$)—CH$_2$—), 2.61 (1H, dd, J=17.2, 4.4 Hz, =C(—OCH$_3$)—CH$_2$—); $^{13}$C NMR (100 MHz, CDCl$_3$): δ 172.3, 166.7, 133.5, 131.1, 130.6, 128.7, 128.6, 128.5, 126.3, 125.9, 125.5, 124.1, 123.6, 122.8, 90.6, 75.9, 56.1, 33.4; ESI-MS (positive): m/z 303 (M+23)$^+$.

Example 21

6-((1E,3E)-4-benzo[d][1,3]dioxol-5-yl)buta-1,3-dienyl)-4-methoxy-5,6-dihydro-2H-pyran-2-one (Compound 76)

Yield: 65%, TLC (EtOAc:Hexane=1:1) Rf=0.36, Pale brown solid, $^1$H NMR (400 MHz, CDCl$_3$): δ 6.93 (1H, d, J=1.6 Hz, Ar—), 6.81 (1H, dd, J=8.0, 1.6 Hz, Ar—), 6.75 (1H, d, J=8.0 Hz, Ar—), 6.44-6.58 (2H, m, Ar—), 5.95 (2H, s, —OCH$_2$O—), 5.80 (1H, 2d, J=6.4 Hz, Ar—CH=CH—CH=CH), 5.17 (1H, d, J=1.3 Hz, —C(=O)—CH=C—), 4.99-4.93 (1H, m, —O—CH(CH=)—CH$_2$), 3.75 (3H, s, —OCH$_3$), 2.59 (1H, ddd, J=17.1, 10.8, 1.3 Hz, =C(—OCH$_3$)—CH$_2$—), 2.47 (1H, dd, J=17.1, 4.4 Hz, =C(—OCH$_3$)—CH$_2$—); $^{13}$CNMR (100 MHz, CDCl$_3$): δ 172.3, 166.8, 148.1, 147.6, 135.8, 134.3, 133.5, 131.2, 128.2, 126.9, 125.6, 121.7, 108.4, 105.5, 101.1, 90.54, 75.7, 56.0, 32.2; ESI-MS (positive): m/z 301 (M+1)$^+$.

Example 22

Synthesis of (E)-6-{2-(benzo[d][1,3]dioxol-5-yl)vinyl}-4-hydroxy-5,6-dihydro-2H-pyran-2-one (Compound 47)

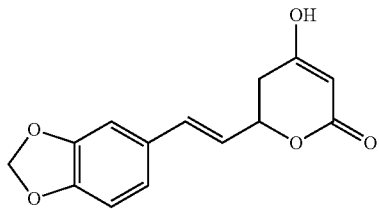

Yield: 62%, TLC (EtOAc:Hexane=9:1) Rf=0.21, Pale yellow solid, $^1$H NMR (400 MHz, DMSO-d$_6$): δ 11.49 (1H, —OH), 7.14 (1H, s, Ar—), 6.93-6.85 (2H, m, Ar—), 6.61 (1H, d, J=15.8 Hz, Ar—CH=CH—), 6.27 (1H, dd, J=15.8, 6.3 Hz, Ar—CH=CH—), 6.02 (2H, s, —OCH$_2$O—), 5.06-4.92 (2H, m, —O—CH(CH=)—CH$_2$—& —C(=O)—CH=C—), 2.65-2.56 (1H, m, =C(—OCH$_3$)—CH$_2$—), 2.48-2.42 (1H, m, =C(—OCH$_3$)—CH$_2$—); $^{13}$C NMR (100 MHz, DMSO-d$_6$): δ 173.3, 167.5, 148.7, 148.2, 132.6, 131.1, 126.0, 122.6, 109.2, 106.5, 102.0, 91.7, 76.1, 33.7; ESI-MS (positive): m/z 282 (M+Na)$^+$.

Preparation of (E)-Ethyl 7-(benzo[d][1,3]dioxol-5-yl)-5-hydroxy-3-oxohept-6-enoate

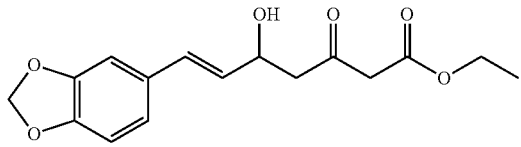 [SMILES: CCOC(=O)CC(=O)CC(O)/C=C/c1ccc2c(c1)OCO2]

Yield: 74%, TLC (EtOAc:Hexane=1:1) Rf=0.30, Pale yellow liquid, $^1$H NMR (400 MHz, CDCl$_3$): δ 6.87 (1H, d, J=1.5 Hz, Ar—), 6.77 (1H, dd, J=8.0, 1.5 Hz, Ar—), 6.71 (1H, d, J=8.0 Hz, Ar—), 6.52 (1H, d, J=15.8 Hz, Ar—CH=CH—), 6.01 (1H, dd, J=15.8, 6.2 Hz, Ar—CH=CH—), 5.92 (2H, s, —OCH$_2$O—), 4.78-4.66 (1H, m, =CH—CH(OH)—CH$_2$—), 4.17 (2H, q, J=7.2 Hz, C(=O)—OCH$_2$—CH$_3$) 3.48 (2H, s, C(=O)—CH$_2$—COOCH$_2$CH$_3$), 2.84-2.80 (2H, m, CH(OH)—CH$_2$—C=O), 1.25 (3H, t, J=7.2 Hz, —COOCH$_2$CH$_3$); $^{13}$C NMR (100 MHz, CDCl$_3$): δ 203.0, 167.2, 148.3, 147.7, 131.1, 130.8, 128.3, 121.3, 108.6, 106.0, 101.4, 68.7, 61.9, 50.3, 49.9, 14.4; ESI-MS (positive): m/z 329 (M+Na)$^+$.

Example 23

Synthesis of (E)-6-{2-(benzo[d][1,3]dioxol-5-yl)vinyl}-4-ethoxy-5,6-dihydro-2H-pyran-2-one (Compound 48)

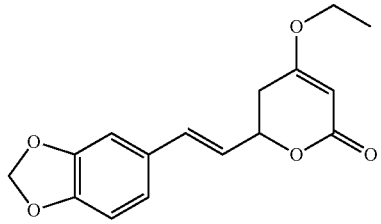 [SMILES: CCOC1=CC(=O)OC(/C=C/c2ccc3c(c2)OCO3)C1]

Yield: 68%, TLC (EtOAc:Hexane=1:1) Rf=0.35, Pale yellow solid, $^1$H NMR (400 MHz, CDCl$_3$): δ 6.92 (1H, d, J=1.5 Hz, Ar—), 6.83 (1H, dd, J=8.0, 1.5 Hz, Ar—), 6.76 (1H, d, J=8.0 Hz, Ar—), 6.63 (1H, d, J=15.8 Hz, Ar—CH=CH—), 6.08 (1H, dd, J=15.8, 6.2 Hz, Ar—CH=CH—), 5.96 (2H, s, —OCH$_2$O—), 5.15 (1H, d, J=1.2 Hz, —C(=O)—CH=C—), 5.06-4.97 (1H, m, —O—CH(CH=)—CH$_2$), 3.99-3.94 (2H, m, —OCH$_2$CH3), 2.64 (1H, ddd, J=17.0, 10.9, 1.4 Hz, =C(—OCH$_3$)—CH$_2$—), 2.51 (1H, dd, J=17.0, 4.4 Hz, =C(—OCH$_3$)—CH$_2$—), 1.4 (3H, t, J=7.0 Hz, —OCH$_2$CH$_3$). $^{13}$C NMR (100 MHz, CDCl$_3$): δ 171.4, 166.9, 148.1, 147.8, 132.8, 130.2, 123.4, 121.7, 108.3, 105.8, 101.2, 90.7, 75.9, 64.8, 33.6, 14.0; ESI-MS (positive): m/z 310. (M+Na)$^+$.

Example 24

Synthesis of (E)-6-(2-(2,3-dihydro-1H-inden-5-yl)vinyl)-4-methoxy-5,6-dihydro-2H-pyran-2-one (Compound 49)

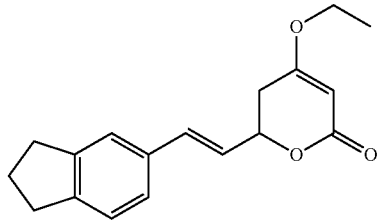 [SMILES: CCOC1=CC(=O)OC(/C=C/c2ccc3c(c2)CCC3)C1]

Yield: 72%, TLC (EtOAc:Hexane=1:1) Rf=0.42, White solid, $^1$H NMR (400 MHz, CDCl$_3$): δ 7.27 (1H, s, Ar—), 7.20-7.12 (2H, m, Ar—), 6.71 (1H, d, J=15.8 Hz, Ar—CH=CH—), 6.20 (1H, dd, J=15.8, 6.3 Hz, Ar—CH=CH—), 5.19 (1H, d, J=1.2 Hz, —C(=O)—CH=C—), 5.07-5.01 (1H, m, —O—CH(CH=)—CH$_2$), 3.76 (3H, s, —OCH$_3$), 2.89 (4H, t, J=7.3 Hz, Ar—CH$_2$—CH$_2$—CH$_2$—Ar), 2.65 (1H, ddd, J=17.0, 10.8, 1.4 Hz, =C(—OCH$_3$)—CH$_2$—), 2.53 (1H, dd, J=17.0, 4.3 Hz, =C(—OCH$_3$)—CH$_2$—), 2.12-2.02 (2H, m, Ar—CH$_2$—CH$_2$—CH$_2$—Ar); $^{13}$C NMR (100 MHz, CDCl$_3$): δ 172.3, 166.8, 144.86, 144.81, 133.8, 133.6, 125.0, 124.5, 124.2, 122.4, 90.5, 76.1, 56.0, 33.4, 32.69, 32.68, 25.4; ESI-MS (positive): m/z 292 (M+Na)$^+$.

Example 25

Synthesis of (E)-6-(2-(2,3-dihydro-1H-inden-5-yl)vinyl)-4-ethoxy-5,6-dihydro-2H-pyran-2-one (Compound 50)

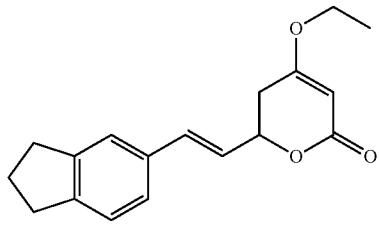 [SMILES: CCOC1=CC(=O)OC(/C=C/c2ccc3c(c2)CCC3)C1]

Yield: 69%, TLC (EtOAc:Hexane=1:1) Rf=0.425, White solid, $^1$H NMR (400 MHz, CDCl$_3$): δ 7.27 (1H, s, Ar—), 7.20-7.12 (2H, m, Ar—), 6.71 (1H, d, J=15.8 Hz, Ar—CH=CH—), 6.20 (1H, dd, J=15.8, 6.3 Hz, Ar—CH=CH—), 5.19 (1H, d, J=1.2 Hz, —C(=O)—CH=C—), 5.07-5.01 (1H, m, —O—CH(CH=)—CH$_2$), 4.02-3.92 (2H, m, —OCH$_2$CH3), 2.89 (4H, t, J=7.3 Hz, Ar—CH$_2$—CH$_2$—CH$_2$—Ar), 2.63 (1H, ddd, J=17.0, 10.8, 1.4 Hz, =C(—OCH$_3$)—CH$_2$—), 2.52 (1H, dd, J=17.0, 4.3 Hz, =C(—OCH$_3$)—CH$_2$—), 2.12-2.02 (2H, m, Ar—CH$_2$—CH$_2$—CH$_2$—Ar), 1.39 (3H, t, J=7.0 Hz, —OCH$_2$CH$_3$); $^{13}$C NMR (100 MHz, CDCl$_3$): δ 171.5, 167.0, 144.82, 144.80, 133.9, 133.5, 125.0, 124.5, 124.3, 122.4, 90.7, 76.1, 64.2, 33.8, 32.69, 32.68, 25.4, 14.0; ESI-MS (positive): m/z 285 (M+1)$^+$.

Example 26

Synthesis of (E)-6-(3-hydroxystyryl)-4-methoxy-5,6-dihydro-2H-pyran-2-one (Compound 51)

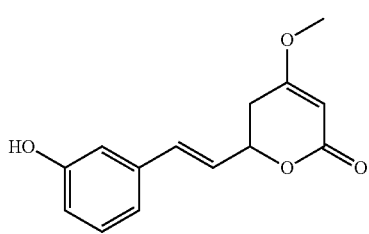 [SMILES: COC1=CC(=O)OC(/C=C/c2cccc(O)c2)C1]

Yield: 63%, TLC (EtOAc:Hexane=1:1) Rf=0.28, White solid, $^1$H NMR (400 MHz, MeOH-D$_4$): 7.15 (1H, t, J=8.0 Hz, Ar—), 6.93-6.85 (2H, m), 6.73-6.66 (2H, m, Ar— & Ar—CH=CH—), 6.29 (1H, dd, J=15.9, 6.3 Hz, Ar—CH=CH—), 5.25 (1H, d, J=1.2 Hz, —C(=O)—CH=C—), 5.15-5.07 (1H, m, —O—CH(CH=)—CH$_2$), 3.82 (3H, s, —OCH$_3$), 2.71 (1H, ddd, J=17.0, 10.9, 1.2 Hz, =C(—OCH$_3$)—CH$_2$—), 2.63 (1H, dd, J=17.09, 4.4 Hz, =C(—OCH$_3$)—CH$_2$—); $^{13}$C NMR (100 MHz, MeOH-D$_4$): δ 175.7, 170.07, 158.8, 138.7, 134.6, 130.6, 126.6, 119.3, 116.4, 114.2, 90.4, 78.0, 57.0, 34.0; ESI-MS (positive): m/z 269 (M+Na)$^+$.

Example 27

Synthesis of (E)-6-(3-hydroxy-4-methoxystyryl)-4-methoxy-5,6-dihydro-2H-pyran-2-one (Compound 52)

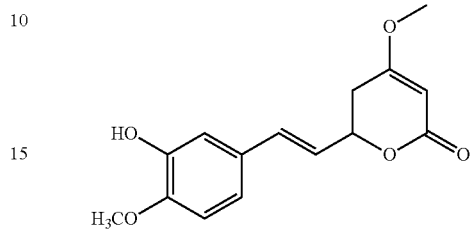

Yield: 52%, TLC (EtOAc:Hexane=1:1) Rf=0.29, White solid, $^1$H NMR (400 MHz, MeOH-D$_4$): δ 6.95 (1H, brs, Ar—), 6.91-6.88 (2H, m, Ar—), 6.65 (1H, d, J=15.8, Ar—CH=CH—), 6.17 (1H, dd, J=15.8, 6.5 Hz, Ar—CH=CH—), 5.25 (1H, d, J=1.26, Hz, —C(=O)—CH=C—), 5.13-5.05 (1H, m, —O—CH(CH=)—CH$_2$), 3.87 ((3H, s, Ar—OCH$_3$), 3.83 (3H, s, —OCH$_3$), 2.74 (1H, ddd, J=17.0, 10.8, 1.3 Hz, =C(—OCH$_3$)—CH$_2$—), 2.61 (1H, dd, J=17.09, 4.4 Hz, =C(—OCH$_3$)—CH$_2$—); $^{13}$C NMR (100 MHz, MeOH-D$_4$): δ 174.3, 167.6, 149.7, 147.8, 133.2, 129.6, 123.0, 118.8, 112.5, 111.1, 89.9, 76.9, 55.5, 54.7, 32.7; ESI-MS (positive): m/z 299 (M+Na)$^+$.

Preparation of (E)-2-hydroxy-4(2-(4-methoxy-6-oxo-3,6-dihydro-2H-pyran2-yl)vinyl) phenylacetate

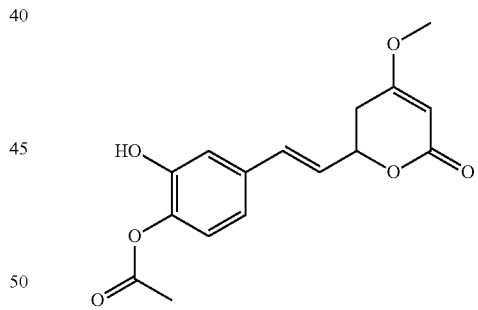

Yield: 54%, TLC (EtOAc:Hexane=1:1) Rf=0.28, White solid, $^1$H NMR (400 MHz, CDCl$_3$): δ 7.69 (1H, s, —ArOH), 7.07-7.05 (1H, brs, Ar—), 6.99-6.90 (2H, m, Ar—), 6.68 (1H, d, J=15.8 Hz, Ar—CH=CH—), 6.12 (1H, dd, J=15.8, 6.2 Hz, Ar—CH=CH—), 5.19 (1H, d, J=1.2 Hz, —C(=O)—CH=C—), 5.07-5.00 (1H, m, —O—CH(CH=)—CH$_2$), 3.77 (3H, s, —OCH$_3$), 2.66 (1H, ddd, J=17.0, 10.8, 1.3 Hz, =C(—OCH$_3$)—CH$_2$—), 2.52 (1H, dd, J=17.0, 4.3 Hz, =C(—OCH$_3$)—CH$_2$—), 2.11 (3H, s, ArOCH$_3$); $^{13}$C NMR (100 MHz, CDCl$_3$): δ 172.2, 168.8, 166.6, 164.2, 144.3, 132.4, 131.2, 124.6, 122.3, 112.9, 109.2, 90.57, 75.7, 56.1, 33.3, 21.0; ESI-MS (negative): m/z 261 (M-43).

Example 28

Synthesis of (E)-6-{2-(benzo[d][1,3]dioxol-5-yl)vinyl}-4-methoxy-5-methyl-5,6-dihydro-2H-pyran-2-one (Compound 53)

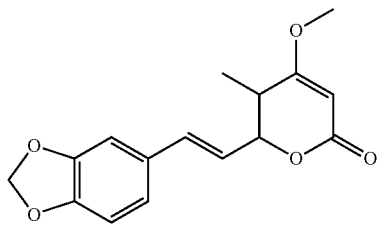 [SMILES: COC1=CC(=O)OC(/C=C/c2ccc3c(c2)OCO3)C1C]

Title compound was obtained as a diasteromeric mixture (58:42). Yield: 68%, TLC (EtOAc:Hexane=1:1) Rf=0.43, White solid, $^1$H NMR (400 MHz, CDCl$_3$): δ 6.93 (1H, d, J=1.6 Hz, Ar—), 6.91 (1H, d, J=1.6 Hz, Ar—), 6.85-6.80 (2H, m, Ar—), 6.78-6.73 (2H, m, Ar—), 6.69 (1H, d, J=15.8 Hz, Ar—CH=CH—), 6.60 (1H, d, J=15.8 Hz, Ar—CH=CH—), 6.1-5.97 (2H, m, Ar—CH=CH—), 5.95 (2H, s, —OCH$_2$O—), 5.94 (2H, s, —OCH$_2$O—), 5.14 (1H, s, —C(=O)—CH=C—), 5.12 (1H, s, —C(=O)—CH=C—), 5.06-5.01 (1H, m, —O—CH(CH=)—CH$_2$), 4.68-4.62 (1H, m, —O—CH(CH=)—CH$_2$), 3.75 (3H, s, —OCH$_3$), 3.72 (3H, s, —OCH$_3$), 2.64-2.57 (1H, m, =C(—OCH$_3$)—CH$_2$—), 2.51-2.43 (1H, m, —C(CH$_3$)—C(—OCH$_3$) (=C)—), 1.25-1.20 (3H, m, —C(CH$_3$)—C(—OCH$_3$) (=C)—), 1.16 (3H, d, J=7.2 Hz, —C(CH$_3$)—C(—OCH$_3$) (=C)—); $^{13}$C NMR (100 MHz, CDCl$_3$): δ 178.6, 175.6, 167.1, 166.5, 148.4, 148.1, 148.0, 134.6, 133.3, 130.7, 130.5, 123.7, 122.1, 121.9, 121.8, 108.7, 108.6, 106.18, 106.1, 101.54, 101.53, 90.1, 89.6, 82.5, 79.2, 56.5, 37.76, 37.52, 14.1, 11.8; ESI-MS (positive): m/z 311 (M+Na)$^+$.

Example 29

Synthesis of (E)-6-{2-(benzo[d][1,3]dioxol-5-yl)vinyl}-4-ethoxy-5-methyl-5,6-dihydro-2H-pyran-2-one (Compound 54)

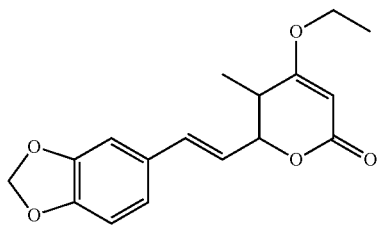 [SMILES: CCOC1=CC(=O)OC(/C=C/c2ccc3c(c2)OCO3)C1C]

Title compound was obtained as a diasteromeric mixture (58:42). Yield: 66%, TLC (EtOAc:Hexane=1:1) Rf=0.45, White solid, $^1$H NMR (400 MHz, CDCl$_3$): δ 6.93 (1H, d, J=1.6 Hz, Ar—), 6.91 (1H, d, J=1.6 Hz, Ar—), 6.85-6.80 (2H, m, Ar—), 6.78-6.74 (2H, m, Ar—), 6.69 (1H, d, J=15.8 Hz, Ar—CH=CH—), 6.60 (1H, d, J=15.8 Hz, Ar—CH=CH—), 6.08-5.96 (2H, m, Ar—CH=CH—), 5.94 (2H, s, —OCH$_2$O—), 5.94 (2H, s, —OCH$_2$O—), 5.10 (1H, s, —C(=O)—CH=C—), 5.08 (1H, s, —C(=O)—CH=C—), 5.06-5.02 (1H, m, —O—CH(CH=)—CH$_2$), 4.67-4.63 (1H, m, —O—CH(CH=)—CH$_2$), 4.03-3.88 (4H, m, —OCH$_2$CH$_3$), 2.62-2.55 (1H, m, =C(—OCH$_3$)—CH$_2$—), 2.49-2.42 (1H, m, —C(CH$_3$)—C(—OCH$_3$) (=C)—), 1.39 (6H, 2t, J=7.1 Hz, —OCH$_2$CH$_3$), 1.26-1.21 (3H, m, —C(CH$_3$)—C(—OCH$_3$) (=C)—), 1.16 (3H, d, J=7.2 Hz, —C(CH$_3$)—C(—OCH$_3$) (=C)—); $^{13}$C NMR (100 MHz, CDCl$_3$): δ177.7, 174.8, 167.3, 166.7, 148.4, 148.1, 148.0, 134.5, 133.1, 130.8, 130.5, 123.8, 122.08, 122.0, 121.9, 108.69, 108.66, 106.1, 106.0, 101.53, 101.52, 90.2, 89.7, 82.4, 79.1, 65.21, 65.17, 37.91, 47.60, 14.34, 14.29, 11.8; ESI-MS (positive): m/z 325 (M+Na)$^+$.

Example 30

Synthesis of (E)-6-{2-(benzo[d][1,3]dioxol-5-yl)vinyl}-4-methoxy-3-methyl-5,6-dihydro-2H-pyran-2-one (Compound 55)

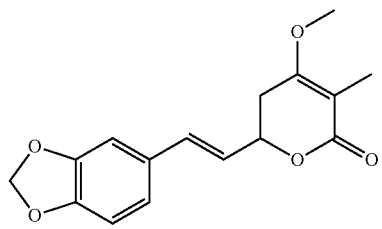 [SMILES: COC1=C(C)C(=O)OC(/C=C/c2ccc3c(c2)OCO3)C1]

Yield: 67%, TLC (EtOAc:Hexane=1:1) Rf=0.42, Pale yellow solid, $^1$H NMR (400 MHz, CDCl$_3$): δ 6.91 (1H, d, J=1.59 Hz, Ar—), 6.82 (1H, dd, J=8.0, 1.4 Hz, Ar—), 6.76 (1H, d, J=8.0 Hz, Ar—), 6.60 (1H, d, J=15.8 Hz, Ar—CH=CH—), 6.1 (1H, dd, J=15.8, 6.4 Hz, Ar—CH=CH—), 5.96 (2H, s, —OCH$_2$O—), 4.96-4.90 (1H, m, —O—CH(CH=)—CH$_2$), 3.8 (3H, s, —OCH$_3$), 2.75-2.59 (2H, m, =C(—OCH$_3$)—CH$_2$—), 1.81 (3H, s, —C(=O)—C(CH$_3$)=C—); $^{13}$C NMR (100 MHz, CDCl$_3$): δ 168.0, 164.9, 148.1, 147.8, 132.9, 130.1, 123.6, 121.7, 108.3, 105.7, 103.7, 101.2, 74.8, 55.5, 29.8, 8.9; ESI-MS (positive): m/z 311 (M+Na)$^+$.

Example 31

Synthesis of (E)-6-{2-(benzo[d][1,3]dioxol-5-yl)vinyl}-4-ethoxy-3-methyl-5,6-dihydro-2H-pyran-2-one (Compound 56)

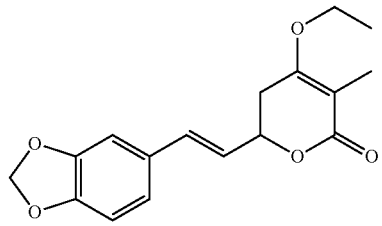 [SMILES: CCOC1=C(C)C(=O)OC(/C=C/c2ccc3c(c2)OCO3)C1]

Yield: 72%, TLC (EtOAc:Hexane=1:1) Rf=0.45, Pale yellow solid, $^1$H NMR (400 MHz, CDCl$_3$): δ 6.91 (1H, d, J=1.6 Hz, Ar—), 6.82 (1H, dd, J=8.0, 1.4 Hz, Ar—), 6.76 (1H, d, J=8.0 Hz, Ar—), 6.64 (1H, d, J=15.8 Hz, Ar—CH=CH—), 6.1 (1H, dd, J=15.8, 6.4 Hz, Ar—CH=CH—), 5.96 (2H, s, —OCH₂O—), 4.96-4.90 (1H, m, —O—CH(CH=)—CH₂), 4.1-3.94 (2H, m, —OCH₂CH₃), 2.73-2.59 (2H, m, =C(—OCH₃)—CH₂—), 1.81 (3H, s, —C(=O)—C(CH₃)=C—), 1.36 (3H, t, J=7.0 Hz, —OCH₂CH₃); ¹³C NMR (100 MHz, CDCl₃): δ 168.1, 164.4, 148.1, 147.8, 132.8, 130.1, 123.9, 121.7, 108.3, 105.7, 103.9, 101.2, 74.9, 64.0, 30.3, 29.6, 15.2, 9.0; ESI-MS (positive): m/z 325 (M+Na)⁺.

Example 32

Synthesis of (E)-6-{2-(benzo[d][1,3]dioxol-5-yl)vinyl}-4-methoxy-6-methyl-5,6-dihydro-2H-pyran-2-one (Compound 57)

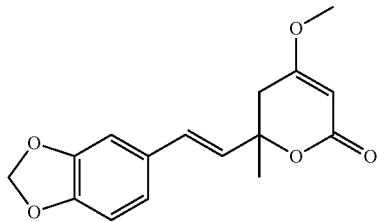 [SMILES: COC1=CC(=O)OC(C)(/C=C/c2ccc3c(c2)OCO3)C1]

Yield: 62%, TLC (EtOAc:Hexane=1:1) Rf=0.42, Pale yellow solid, ¹H NMR (400 MHz, CDCl₃): δ 6.88 (1H, d, J=1.6 Hz, Ar—), 6.79 (1H, dd, J=8.0, 1.6 Hz, Ar—), 6.76 (1H, d, J=8.0 Hz, Ar—), 6.52 (1H, d, J=16.1 Hz, Ar—CH=CH—), 6.02 (1H, d, J=16.1 Hz, Ar—CH=CH—), 5.94 (2H, s, —OCH₂O—), 5.15 (1H, d, J=1.2 Hz, —C(=O)—CH=C—), 3.72 (3H, s, —OCH₃), 2.69 (1H, dd, J=1.2, 16.9 Hz, =C(—OCH₃)—CH₂—), 2.59 (1H, d, J=16.9 Hz, =C(—OCH₃)—CH₂—), 1.59 (3H, s, -, —O—C(CH₃)(CH=)—CH₂—); ¹³C NMR (100 MHz, CDCl₃): δ 171.1, 166.6, 148.0, 147.5, 130.3, 129.3, 129.1, 121.5, 108.3, 105.7, 101.1, 90.4, 79.4, 55.9, 38.1, 27.7; ESI-MS (positive): m/z 311 (M+Na)⁺.

Example 33

Synthesis of (E)-6-{2-(benzo[d][1,3]dioxol-5-yl)vinyl}-4-butoxy-5,6-dihydro-2H-pyran-2-one (Compound 58)

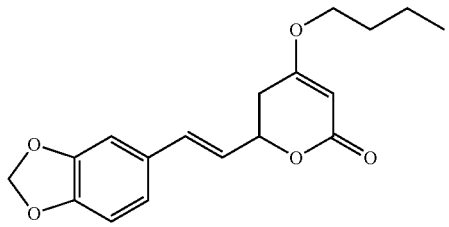 [SMILES: CCCCOC1=CC(=O)OC(/C=C/c2ccc3c(c2)OCO3)C1]

Yield: 68%, TLC (EtOAc:Hexane=1:1) Rf=0.43, Pale yellow solid, ¹H NMR (400 MHz, CDCl₃): δ 6.92 (1H, d, J=1.5 Hz, Ar—), 6.82 (1H, dd, J=8.0, 1.5 Hz, Ar—), 6.76 (1H, d, J=8.0 Hz, Ar—), 6.62 (1H, d, J=15.8 Hz, Ar—CH=CH—), 6.08 (1H, dd, J=15.8, 6.2 Hz, Ar—CH=CH—), 5.96 (2H, s, —OCH₂O—), 5.15 (1H, d, J=1.2 Hz, —C(=O)—CH=C—), 5.05-4.98 (1H, m, —O—CH(CH=)—CH₂), 3.92-3.88 (2H, m, OCH₂CH₂CH₂CH₃), 2.64 (1H, ddd, J=17.0, 10.9, 1.4 Hz, =C(—OCH₃)—CH₂—), 2.51 (1H, dd, J=17.0, 4.4 Hz, =C(—OCH₃)—CH₂—), 1.78-1.68 (2H, m, —OCH₂CH₂CH₂CH₃), 1.50-1.38 ((2H, m, —OCH₂CH₂CH₂CH₃), 0.96 (3H, t, J=7.3 Hz, —OCH₂CH₂CH₂CH₃); ¹³C NMR (100 MHz, CDCl₃): δ 171.6, 166.9, 148.1, 147.8, 132.8, 130.2, 123.7, 121.7, 108.3, 105.8, 101.2, 90.7, 75.9, 68.9, 33.6, 30.4, 19.0, 13.6; ESI-MS (positive): m/z 317 (M+1)⁺.

Example 34

Synthesis of (E)-6-{2-(benzo[d][1,3]dioxol-5-yl)vinyl}-4-(benzyloxy)-5,6-dihydro-2H-pyran-2-one (Compound 59)

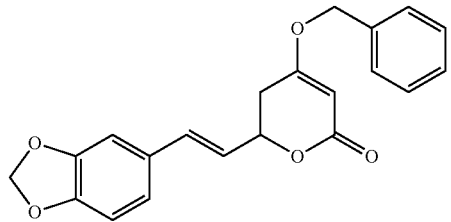 [SMILES: O=C1C=C(OCc2ccccc2)CC(/C=C/c2ccc3c(c2)OCO3)O1]

Yield: 68%, TLC (EtOAc:Hexane=1:1) Rf=0.41, Pale yellow solid, ¹H NMR (400 MHz, CDCl₃): δ 7.45-7.33 (5H, m, —OCH₂C₆H₅), 6.92 (1H, d, J=1.5 Hz, Ar—), 6.82 (1H, dd, J=8.0, 1.5 Hz, Ar—), 6.76 (1H, d, J=8.0 Hz, Ar—), 6.64 (1H, d, J=15.8 Hz, Ar—CH=CH—), 6.09 (1H, dd, J=15.8, 6.2 Hz, Ar—CH=CH—), 5.96 (2H, s, —OCH₂O—), 5.30 (1H, d, J=1.2 Hz, —C(=O)—CH=C—), 5.09-5.01 (1H, m, —O—CH(CH=)—CH₂), 4.96 (2H, s, —OCH₂C₆H₅), 2.71 (1H, ddd, J=17.0, 10.9, 1.4 Hz, =C(—OCH₃)—CH₂—), 2.59 (1H, dd, J=17.0, 4.4 Hz, =C(—OCH₃)—CH₂—); ¹³C NMR (100 MHz, CDCl₃): δ 171.1, 166.6, 148.1, 147.8, 134.4, 133.0, 130.1, 128.8, 127.9, 123.6, 121.7, 108.3, 105.8, 101.2, 91.7, 76.0, 71.0, 33.5; ESI-MS (positive): m/z 351 (M+1)⁺.

Example 35

Synthesis of (E)-6-{2-(benzo[d][1,3]dioxol-5-yl)vinyl}-4-propoxy-5,6-dihydro-2H-pyran-2-one (Compound 60)

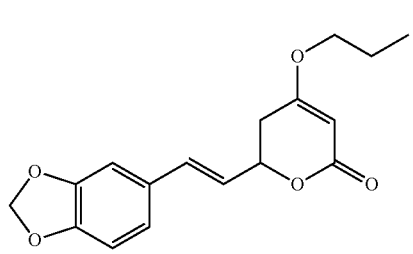 [SMILES: CCCOC1=CC(=O)OC(/C=C/c2ccc3c(c2)OCO3)C1]

Yield: 64%, TLC (EtOAc:Hexane=1:1) Rf=0.42, Pale yellow solid, ¹H NMR (400 MHz, CDCl₃): δ 6.91 (1H, d, J=1.5 Hz, Ar—), 6.82 (1H, dd, J=8.0, 1.5 Hz, Ar—), 6.76 (1H, d, J=8.0 Hz, Ar—), 6.62 (1H, d, J=15.8 Hz, Ar—CH=CH—), 6.07 (1H, dd, J=15.8, 6.2 Hz, Ar—CH=CH—), 5.95 (2H, s, —OCH₂O—), 5.15 (1H, d, J=1.2 Hz, —C(=O)—CH=C—), 5.04-4.97 (1H, m, —O—CH(CH═)—CH$_2$), 3.87-3.83 (2H, m, —OCH$_2$CH$_2$CH$_3$), 2.64 (1H, ddd, J=17.0, 10.9, 1.4 Hz, ═C(—OCH$_3$)—CH$_2$—), 2.52 (1H, dd, J=17.0, 4.4 Hz, ═C(—OCH$_3$)—CH$_2$—), 1.80-1.74 (2H, m, —OCH$_2$CH$_2$CH$_3$), 1.0 (3H, t, J=7.0 Hz, —OCH$_2$CH$_2$CH$_3$); $^{13}$C NMR (100 MHz, CDCl$_3$): δ 171.6, 166.9, 148.1, 147.8, 132.8, 130.2, 123.7, 121.7, 108.3, 105.8, 101.2, 90.7, 75.9, 70.6, 33.5, 22.6, 10.3; ESI-MS (positive): m/z 303 (M+1)$^+$.

Example 36

Synthesis of (E)-6-{2-(benzo[d][1,3]dioxol-5-yl)vinyl}-5,6-dihydro-2H-pyran-2-one (Compound 61)

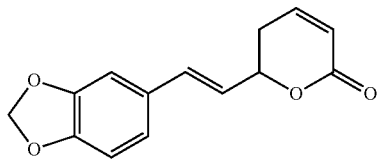 [SMILES: O=C1C=CCC(/C=C/c2ccc3c(c2)OCO3)O1]

Yield: 72%, TLC (EtOAc:Hexane=1:1) Rf=0.58, Pale yellow solid, $^1$H NMR (400 MHz, CDCl$_3$): δ 6.95-6.88 (2H, m, Ar—), 6.83 (1H, dd, J=8.0, 1.5 Hz, Ar—), 6.76 (1H, d, J=8.0 Hz, —O—C(═O)—CH═C—), 6.63 (1H, d, J=15.8 Hz, Ar—CH═CH—), 6.13-6.06 (2H, m, Ar—CH═CH—, C(═O)—CH═CH—), 5.96 (2H, s, —OCH$_2$O—), 5.10-5.03 (1H, m, —O—CH(CH═)—CH$_2$), 2.55-2.49 (2H, m, —C═C—CH$_2$—); $^{13}$C NMR (100 MHz, CDCl$_3$): δ 163.8, 148.1, 147.8, 144.5, 132.9, 130.1, 123.8, 121.73, 121.71, 108.3, 105.8, 101.2, 78.06, 29.95; ESI-MS (positive): m/z 245 (M+1)$^+$.

Example 37

Synthesis of (E)-6-{2-(benzo[d][1,3]dioxol-5-yl)vinyl}-3-methyl-5,6-dihydro-2H-pyran-2-one (Compound 62)

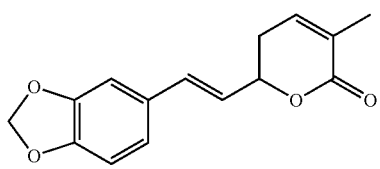 [SMILES: CC1=CCC(/C=C/c2ccc3c(c2)OCO3)OC1=O]

Yield: 23%, TLC (EtOAc:Hexane=1:1) Rf=0.61, Pale yellow solid, $^1$H NMR (400 MHz, CDCl$_3$): δ 6.92 (1H, d, J=1.5 Hz, Ar—), 6.83 (1H, dd, J=8.0, 1.5 Hz, Ar—), 6.76 (1H, d, J=8.0 Hz, Ar—), 6.65-6.57 (2H, m, Ar—CH═CH—, C(═O)—C(—CH$_3$)═CH—), 6.09 (1H, dd, J=15.8, 6.2 Hz, Ar—CH═CH—), 5.96 (2H, s, —OCH$_2$O—), 5.06-4.96 (1H, m, —O—CH(CH═)—CH$_2$), 2.53-2.43 (2H, m, —C═C—CH$_2$—), 1.96 (3H, brs, C(═O)—C(—CH$_3$)═CH—); $^{13}$C NMR (100 MHz, CDCl$_3$): δ 165.5, 148.1, 147.8, 138.4, 132.6, 130.2, 128.8, 124.1, 121.6, 108.3, 105.8, 101.18, 78.16, 30.3, 17.09; ESI-MS (positive): m/z 259 (M+1)$^+$.

Example 38

Synthesis of Representative Compounds of the Invention

The following compounds can be prepared using procedures similar to those described herein.

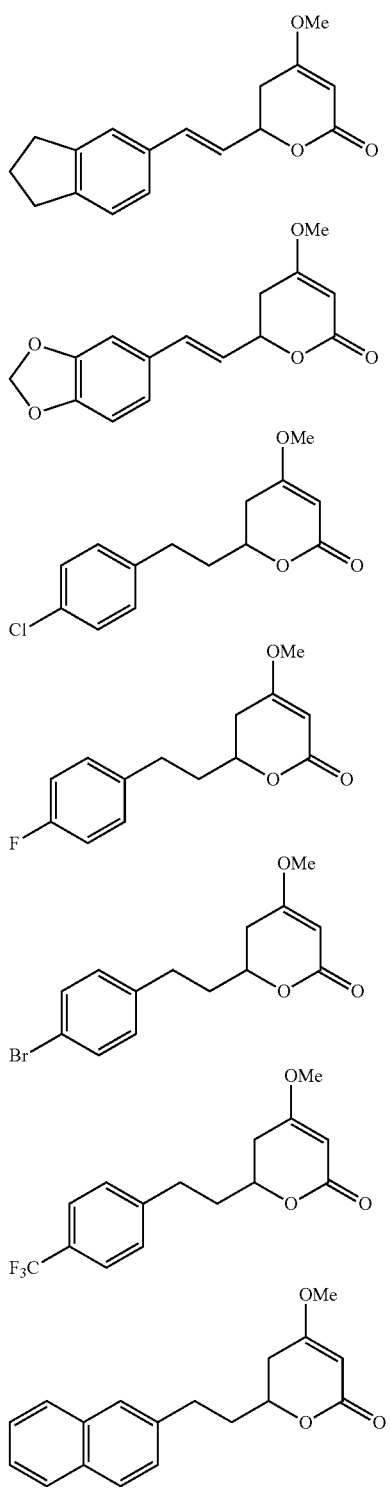

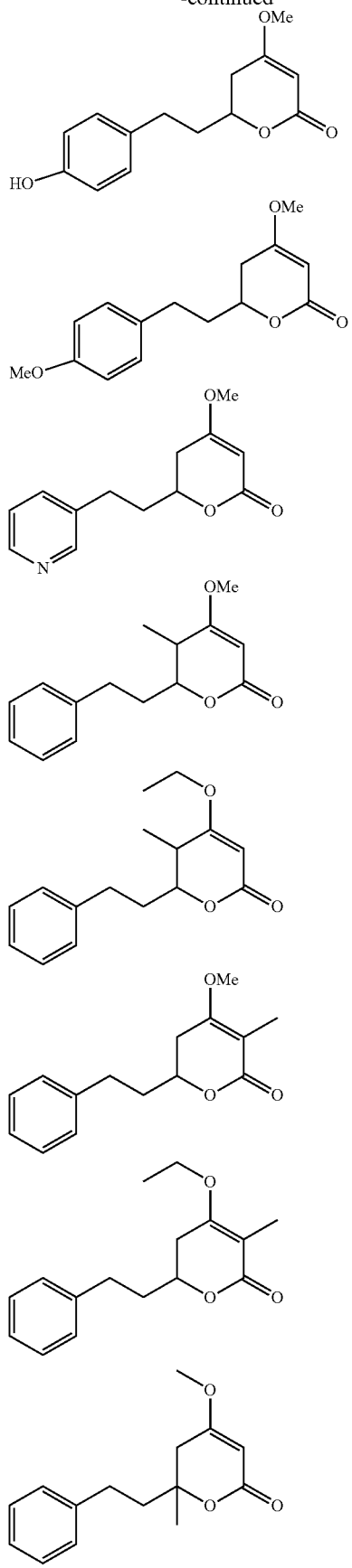
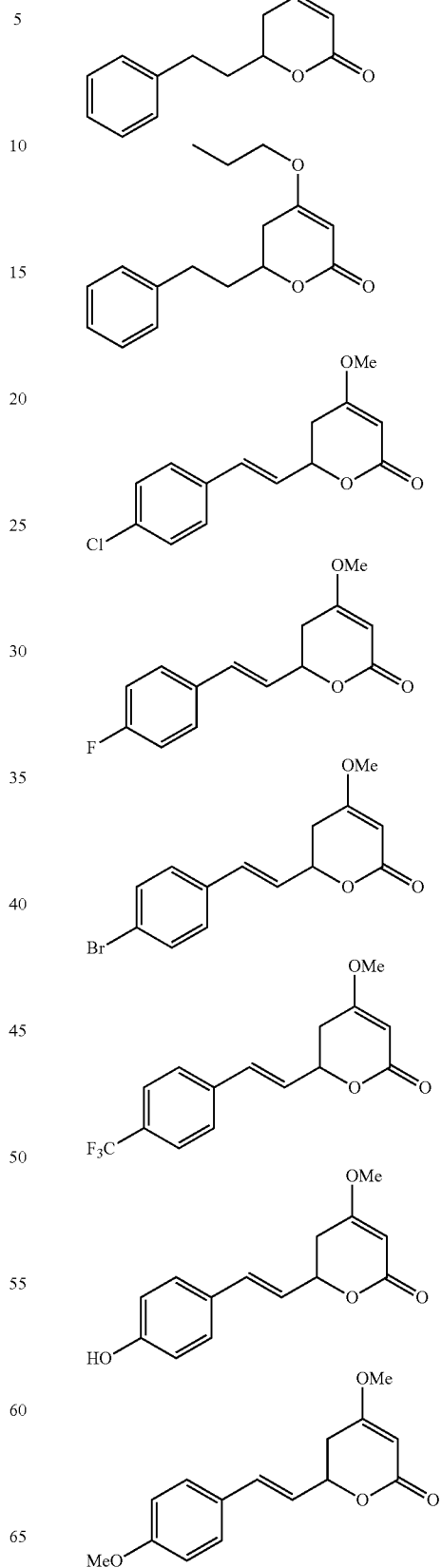

-continued

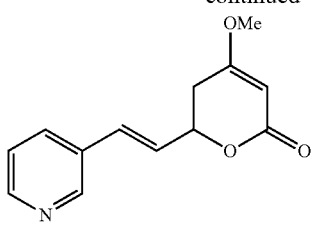
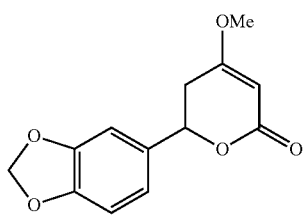
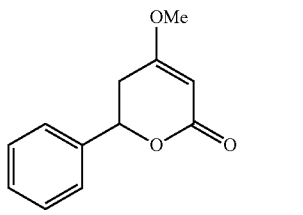
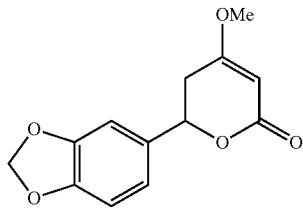
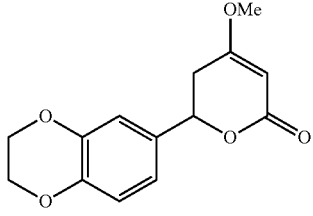
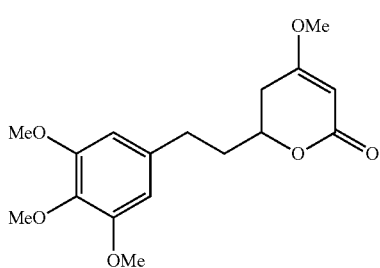
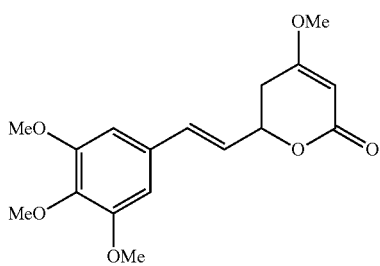

-continued

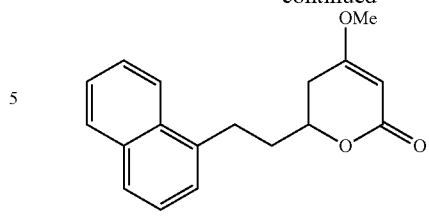
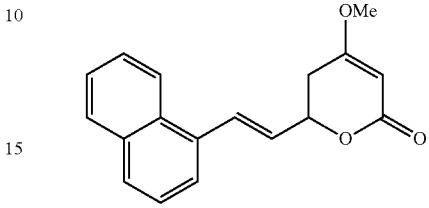
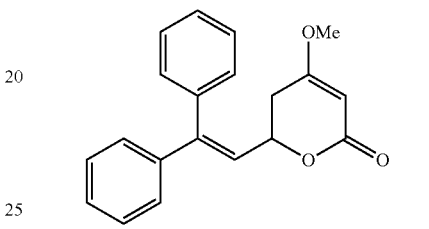

and

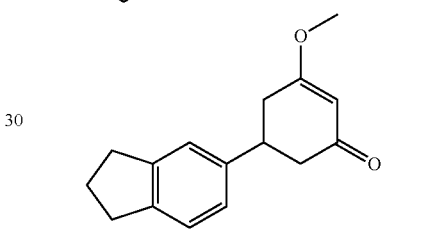

and salts thereof.

Example 39

Dosage Forms

The following illustrate representative pharmaceutical dosage forms, containing 'Compound X', for therapeutic or prophylactic use in humans. As described herein, Compound X may represent a compound described herein.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

-continued

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (vii) Aerosol 1 | mg/can |
|---|---|
| Compound X = | 10.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (viii) Aerosol 2 | mg/can |
|---|---|
| Compound X = | 5.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (ix) Aerosol 3 | mg/can |
|---|---|
| Compound X = | 2.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula (Ic):

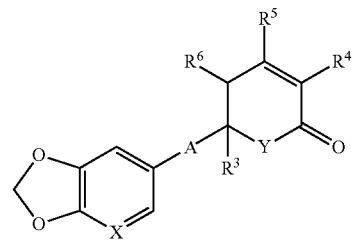

(Ic)

wherein:
the 5-membered ring that comprises two O atoms is optionally substituted with 1 or 2 groups independently selected from halo, hydroxy, cyano, trifluoromethyl, trifluoromethoxy, $(C_1-C_3)$alkyl, and $(C_1-C_3)$alkoxy;
X is CH;
A is —$CH_2CH_2$—, —$CR^b$=CH—, or —CH=CH—CH=CH—;
$R^3$ is H, or $(C_1-C_6)$alkyl;
Y is $CH_2$;
$R^4$ is H, halo, $(C_1-C_6)$alkyl, or $(C_1-C_6)$alkoxy;
$R^5$ is $(C_1-C_6)$alkoxy that is optionally substituted with phenyl;
$R^6$ is H, halo, $(C_1-C_6)$alkyl, or $(C_1-C_6)$alkoxy; and
$R^b$ is H or phenyl that is optionally substituted with 1, 2, or 3 groups independently selected from halo, hydroxy, cyano, trifluoromethyl, trifluoromethoxy, $(C_1-C_3)$alkyl, and $(C_1-C_3)$alkoxy;
or a salt thereof.

2. The compound of claim 1 wherein the 5-membered ring that comprises two O atoms is not substituted.

3. The compound of claim 1 wherein A is —$CH_2CH_2$—.

4. The compound of claim 1 wherein $R^3$ is H.

5. The compound of claim 1 wherein $R^5$ is methoxy, ethoxy, propoxy, benzyloxy, or butoxy.

6. A compound selected from:

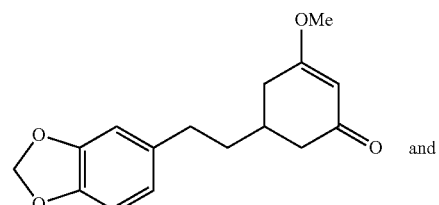

and

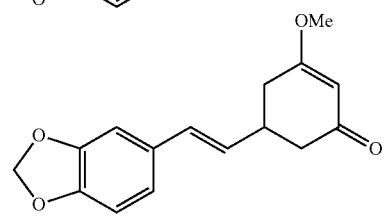

or a salt thereof.

7. A pharmaceutical composition comprising a compound as described in claim 1, or a pharmaceutically acceptable salt thereof, and a pharmaceutically acceptable carrier.

8. The compound of claim 4, wherein A is —$CH_2CH_2$—.

* * * * *